(12) United States Patent
Arrachart et al.

(10) Patent No.: US 9,441,285 B2
(45) Date of Patent: Sep. 13, 2016

(54) BIFUNCTIONAL COMPOUNDS USEFUL AS LIGANDS OF URANIUM (VI), METHODS OF SYNTHESISING SAME AND USES THEREOF

(71) Applicant: AREVA Mines, Courbevoie (FR)

(72) Inventors: Guilhem Arrachart, Saint Laurent des Arbres (FR); Nicolas Aychet, Triel sur Seine (FR); Gilles Bernier, Avignon (FR); Fabien Burdet, Plaisir (FR); Antoine Leydier, Bagnols sur Ceze (FR); Manuel Miguirditchian, Avignon (FR); Stephane Pellet-Rostaing, Villeurbanne (FR); Gabriel Plancque, Paris (FR); Raphael Turgis, Sabran (FR); Elisabeth Zekri, Chatillon (FR)

(73) Assignee: Areva Mines, Courbevoie (FR)

( * ) Notice: Subject to any disclaimer, the term of this patent is extended or adjusted under 35 U.S.C. 154(b) by 0 days.

(21) Appl. No.: 14/399,935

(22) PCT Filed: May 6, 2013

(86) PCT No.: PCT/EP2013/059352
§ 371 (c)(1),
(2) Date: Nov. 7, 2014

(87) PCT Pub. No.: WO2013/167516
PCT Pub. Date: Nov. 14, 2013

(65) Prior Publication Data
US 2015/0133688 A1    May 14, 2015

(30) Foreign Application Priority Data

May 7, 2012    (FR) ...................................... 12 54176
Dec. 19, 2012    (FR) ...................................... 12 62362

(51) Int. Cl.
*C22B 60/02*    (2006.01)
*C07F 9/572*    (2006.01)
(Continued)

(52) U.S. Cl.
CPC ........... *C22B 60/026* (2013.01); *C07F 9/3808* (2013.01); *C07F 9/4006* (2013.01);
(Continued)

(58) Field of Classification Search
CPC .. C07F 9/3808; C07F 9/4006; C07F 9/5722; C22B 60/0243; C22B 60/026; G21F 9/007; G21F 9/06; G21F 9/125
USPC ................................................ 564/15; 423/9
See application file for complete search history.

(56) References Cited

U.S. PATENT DOCUMENTS 3,711,591 A    1/1973 Hurst et al.
4,316,877 A    2/1982 Tunick et al.
(Continued)

FOREIGN PATENT DOCUMENTS

FR    2 396 803 A1    2/1979
FR    2 460 958 A1    1/1981
(Continued)

OTHER PUBLICATIONS

Maheswari ("High performance liquid chromatographic studies on lanthanides, uranium and thorium on amide modified reversed phase supports" Talanta 72(2007), p. 730-740).*
(Continued)

*Primary Examiner* — Jafar Parsa
*Assistant Examiner* — Amy C Bonaparte
(74) *Attorney, Agent, or Firm* — Nixon Peabody LLP; Khaled Shami

(57) ABSTRACT

New compounds which meet general formula (I):

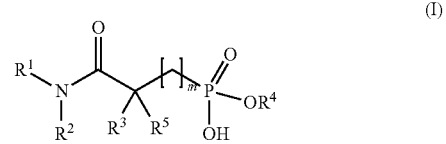

where:
m=0, 1 or 2;
$R^1$ and $R^2$=a $C_6$ to $C_{12}$, straight-chain or branched, hydrocarbon group;
$R^3$=H, a $C_1$ to $C_{12}$, straight-chain or branched, hydrocarbon group, optionally comprising one or more heteroatoms; a $C_3$ to $C_8$ monocyclic hydrocarbon group, optionally comprising one or more heteroatoms, or a monocyclic (hetero)aryl group;
or else $R^2$ and $R^3$ together form a —$(CH_2)_n$— group where n=1 to 4;
$R^4$=a $C_2$ to $C_8$, straight-chain or branched, hydrocarbon group, or a monocyclic aromatic group;
$R^5$=H, or a $C_1$ to $C_{12}$, straight-chain or branched, hydrocarbon group.

25 Claims, 6 Drawing Sheets

(51) Int. Cl.
- C07F 9/38 (2006.01)
- C07F 9/40 (2006.01)
- G21F 9/00 (2006.01)
- G21F 9/06 (2006.01)
- G21F 9/12 (2006.01)

(52) U.S. Cl.
CPC ......... *C07F9/5722* (2013.01); *C22B 60/0243* (2013.01); *G21F 9/007* (2013.01); *G21F 9/06* (2013.01); *G21F 9/125* (2013.01)

(56) References Cited

U.S. PATENT DOCUMENTS 4,525,333 A * 6/1985 Schimmel ............ C01G 15/003
423/112
2014/0030172 A1 1/2014 Bisson et al.

FOREIGN PATENT DOCUMENTS

| FR | 2 460 960 A1 | 1/1981 |
| FR | 2 596 383 A1 | 10/1987 |
| FR | 2 604 919 A1 | 4/1988 |
| SU | 376 387 A1 | 4/1973 |
| WO | 2013/167516 A1 | 11/2013 |

OTHER PUBLICATIONS

Du ("Preparation of a-Phosphono Lactams via Electrophilic Phosphorus Reagents: An Application in the Synthesis of Lactam-Based Farnesyl Transferase Inhibitors" J. Org. Chem. 67(16), 2002, p. 5709-5717).*

Zakrzewska ("Intramolecular C-H insertion catalyzed by dirhodium(II) complexes using CO2 as the reaction media" Green Chemistry Letters and Reviews, vol. 5issue 2, 2012, p. 211-240).*

Bahner, C.T. et al., "Impurities that cause difficulty in stripping actinides from commercial tetraalkylcarbamoylmethylphosphonates", Oak Ridge National Laboratory, Chemical Technology Division, ORNL-5295: Annual Progress Report: Period Ending Mar. 31, 1977, 20 pages, Abstract.

Filippov, E.A. et al., "Organophosphorus pseudo acids in the extraction of protonic and aprotic acids", Raoiokhimiya, vol. 22, Issue 2, 1980, pp. 218-224, Abstract.

Maheswari, M. et al., "Selective enrichment of U(VI), Th(IV) and La(III) from high acidic streams using a new chelating ion-exchange polymeric matrix", Talanta, vol. 64, Issue 1, Apr. 2004, pp. 202-209.

International Search Report and Written Opinion in International Application No. PCT/EP2013/059352, mailed Jun. 28, 2013.

International Preliminary Report on Patentability in International Application No. PCT/EP2013/059352, mailed Apr. 25, 2014.

Search Report in French Application Application No. FR1254176, mailed Jan. 9, 2013.

Bahner, C.T. et al., "Impurities That Cause Difficulty in Stripping Actinides from Commercial Tetraalkylcarbamoylmethylphosphonates", Oak Ridge National Laboratory, Chemical Technology Division, ORNL/TM-5878, Sep. 1977, 27 pages.

French Preliminary Search Report in FR1262362 dated Jun. 12, 2013.

Yarmukhametova, D. KH. et al., "Phosphorylated diphenylamines",1973;1 p.; Database CA [Online] Chemical Abstracts Service, Columbus Ohio, U.S.; XP-002698826; Abstract.

* cited by examiner

BIFUNCTIONAL COMPOUNDS USEFUL AS LIGANDS OF URANIUM (VI), METHODS OF SYNTHESISING SAME AND USES THEREOF

CROSS-REFERENCE TO RELATED PATENT APPLICATIONS

The present application is a national phase application under 35 U.S.C. §371 of International Application No. PCT/EP2013/059352 filed on May 6, 2013 and titled NEW BIFUNCTIONAL COMPOUNDS USEFUL AS LIGANDS OF URANIUM (VI), METHODS OF SYNTHESISING SAME AND USES, which claims benefit of priority to French Patent Application No. 1254176 filed on May 7, 2012, and to French Patent Application No. 1262362filed on Dec. 19, 2012, the contents of which are incorporated herein by reference in their entirety.

TECHNICAL FIELD

The invention relates to the field of uranium extraction from aqueous media containing phosphoric acid.

More specifically, the invention relates to novel bifunctional compounds capable alone (i.e. in the absence of any other extracting molecule) of extracting uranium(VI) from an aqueous solution of phosphoric acid both with high efficiency and with high selectivity versus other metal cations which may be present in this solution and in particular iron(III).

It also relates to methods which allow the synthesis of these bifunctional compounds.

It additionally relates to the uses of these bifunctional compounds as ligands of uranium(VI), and in particular to extract uranium(VI) from an aqueous solution of phosphoric acid such as a solution derived from digestion of a natural phosphate by sulphuric acid.

It further relates to a method which allows the recovery of the uranium contained in an aqueous solution of phosphoric acid derived from digestion of a natural phosphate by sulphuric acid, and which uses said compounds.

The invention finds particular application in the treatment of natural phosphates with a view to recovering the uranium contained in these phosphates.

STATE OF THE PRIOR ART

Natural phosphates (or phosphate ore) used to produce phosphoric acid and fertiliser, contain uranium in contents which may vary from a few tens of ppm to several thousand ppm, as well as variable amounts of other metals.

Nearly all the uranium contained in natural phosphates passes into aqueous solutions of phosphoric acid derived from digestion of these phosphates by sulphuric acid.

The potential recovery of the uranium contained in these phosphate ores amounts to 14000 tonnes/year, i.e. about 25% of the annual production of uranium, thereby representing a non-negligible source of uranium supply.

Therefore numerous research teams have turned their attention to the extraction of uranium from a phosphoric medium.

For economic reasons the recovery of uranium must be obtained from concentrated and not dilute aqueous solutions of phosphoric acid, even if the extraction of uranium would be easier at lower acidity.

The digestion of natural phosphates with sulphuric acid converts tricalcium phosphate to phosphoric acid $H_3PO_4$ with 30% phosphate anhydride $P_2O_5$, and to insoluble calcium sulphate (gypsum). This lixiviation solubilises the uranium and various other metals (iron, vanadium, cadmium, molybdenum, etc.).

With the process used by most industrial units to recover the uranium contained in natural phosphates and which is known as the <<Oak Ridge process>> (since it was developed by the national Oak Ridge laboratory (USA), U.S. Pat. No. 3,711,591, reference [1]), the aqueous flow of phosphoric acid resulting from digestion of the phosphates with sulphuric acid is subjected to an oxidation operation by bubbling (oxygen in the air being used as oxidising agent) or by the addition of an oxidant in particular a solution of sodium chlorate $NaClO_3$ or oxygenated water, to convert the entirety of the uranium to uranium(VI). The temperature of this flow is then brought to 40-45° C. and uranium (VI) is extracted in a first extraction cycle by a synergic mixture of di-(2-ethylhexyl)phosphoric acid (or HDEHP) and trioctylphosphine oxide (or TOPO).

The maximum synergic effect of this mixture for uranium (VI) (and U/Fe selectivity) is obtained in a relative proportion of 4 molecules of HDEHP per 1 molecule of TOPO, and the composition of the reference organic phase is the following: 0.5 mol/L HDEHP+0.125 mol/L TOPO in n-dodecane or an equivalent aliphatic diluent.

The uranium is then stripped with an aqueous phosphoric solution containing $Fe^{2+}$ ions which reduce the uranium(VI) to uranium(IV) thereby promoting its stripping in an aqueous phase. This stripping allows the uranium to be concentrated by a factor of about 70.

In a second extraction cycle, the stripped aqueous flow containing uranium(IV) is in turn subjected to an oxidation reaction to convert the entirety of the uranium contained therein to oxidation state VI, and the uranium(VI) is then extracted with the synergic HDEHP/TOPO mixture.

The organic phase resulting from this extraction is washed with water to remove the extracted phosphoric acid and then subjected to a stripping operation with a solution of ammonium carbonate $(NH_4)_2CO_3$ which in fine leads to the precipitation of ammonium uranyl tricarbonate which, after calcining, yields uranium sesquioxide $U_3O_8$.

When this process issued to purify the uranium contained in natural phosphates with high uranium concentration, various disadvantages are to be noted, namely:
  the distribution coefficients of uranium(VI) prove to be fairly low, which requires the use of strong concentrations of extractants (or strong organic flow rates); and
  non-negligible amounts of iron are extracted despite a high separation factor between uranium and iron ($FS_{U/Fe} \sim 200$), possibly leading to the formation of precipitates during stripping of uranium in a carbonate medium.

In addition, the use of a synergic system with two extractants having an optimum molar ratio to be heeded (4:1) is less easy to manage than a system with a single extractant.

In the 1980's, it was proposed to replace the HDEHP/TOPO synergic mixture with a mixture of bis-(di-n-butoxy-1,3-propyl-2)-phosphoric acid (or HBiDiBOPP) and di-n-hexylmethoxyoctylphosphine oxide (or DinHMOPO) (see French patent applications 2 396 803 and 2 596 383, references [2] and [3]). This mixture leads to higher coefficients of uranium distribution than those obtained with the HDEHP/TOPO mixture, but it also produces high iron extraction and is therefore less selective for uranium.

One way to improve the extraction of uranium from an aqueous solution of phosphoric acid would therefore be to replace the synergic HDEHP/TOPO mixture by grouping together the two functions of <<cation exchanger>> and <<solvating extractant>> within one and the same compound.

A bifunctional compound would have several advantages, namely: the fact that only one single compound needs to be managed instead of two, and the fact that it would become possible to transpose the liquid-liquid extraction system to a solid-liquid extraction system since the properties of a solid on which a single compound is grafted (or adsorbed) are easier to control than the properties of a solid on which two grafted (or adsorbed) compounds act in synergy.

Tunick et al. in U.S. Pat. No. 4,316,877 (reference [4]) proposed extracting uranium from an aqueous solution of phosphoric acid with a di- or triphosphonic acid bearing a $C_8$ to $C_{18}$ alkyl group, with or without the addition of a co-extractant such as tri-n-butylphosphate (or TBP) or di-n-butylbutylphosphonate (or DBBP).

In this reference, the best results are obtained with an organic phase which comprises a triphosphonic acid with nonyl group, TBP (as co-extractant) and kerosene, in a volume ratio of 10:40:50, and which leads to distribution coefficients not exceeding 5.1 for uranium(VI) and close to 157 for uranium(IV).

In addition, the selectivity of the extraction of uranium versus other elements and in particular iron, and the conditions required for subsequent stripping of uranium(VI) from the organic phase are not indicated.

Also, Sturtz in French patent applications 2 460 958 and 2 460 960 (references [5] and [6]), proposed extracting uranium(IV) from an aqueous solution of phosphoric acid using diphosphonates (reference [5]) or triphosphonates (reference [6]). In both cases the uranium(VI) contained in the aqueous solution of phosphoric acid is previously reduced to uranium(IV) via the action of metal iron.

Regarding the diphosphonates, the best results are obtained with an organic phase which comprises a diphosphonate in 97 volume % dilution in kerosene and which leads to a distribution coefficient of 53.6 for uranium(IV) and to uranium/iron selectivity of 151.6, whilst for the triphosphonates the best results are obtained with an organic phase which comprises a triphosphonate, kerosene and chloroform (as co-solvent), in a volume ratio of 3:94.5:2.5, and which leads to a distribution coefficient for uranium(IV) of 25 and for uranium/iron selectivity of 2.5.

There is no mention in these two references on the capacity of the diphosphonates and triphosphonates to extract uranium(VI), and for all the more reason no mention of the conditions required for secondary stripping thereof.

Finally, Warshawsky et al. in French patent application 2 604 919 (reference [7]), proposed a bifunctional compound comprising a phosphine oxide function and a phosphoric or thiophosphoric function, these two functions being linked to one another via an ether, thioether, polyether or polythio-ether spacer group.

This type of compound has two drawbacks. The tests conducted with one of these compounds showed that while this compound is solubilised in n-dodecane, a third phase is formed during extraction of the uranium, whilst if it is solubilised in chloroform, a third phase is similarly formed but during the stripping of the uranium. Yet the onset of a third phase is fully prohibitive for a process intended to be applied on industrial scale. Also, the presence within the spacer group of a P—O or P—S bond, which easily hydrolyses, makes these compounds extremely sensitive to hydrolysis.

Having regard to the foregoing, the Inventors therefore set themselves the objective of providing novel bifunctional compounds which can advantageously be used in lieu and stead of the HDEHP/TOPO synergic system to recover the uranium contained in an aqueous solution of phosphoric acid obtained from a natural phosphate, in particular in that they exhibit greater affinity for uranium(VI) and exhibit further, if possible, lesser affinity for iron (III) and for any other cations which may be contained in this type of solution.

They additionally set themselves the objective that these compounds should be free of the various shortcomings of the bifunctional compounds proposed in the aforementioned references [4] to [7], and in particular of the need for these compounds to be associated with a co-extractant, of the need for prior reducing of uranium(VI) to uranium(IV), of the formation of a third phase and of the risk of hydrolysis.

DESCRIPTION OF THE INVENTION

These objectives and others are reached with the invention which first proposes a compound meeting general formula (I) below:

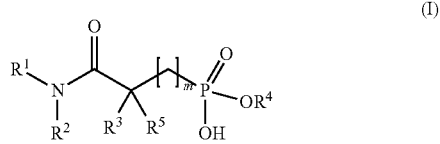

where:
m is an integer of 0, 1 or 2;
$R^1$ and $R^2$, the same or different, are a saturated or unsaturated, straight-chain or branched hydrocarbon group having 6 to 12 carbon atoms;
$R^3$ is:
a hydrogen atom;
a saturated or unsaturated, straight-chain or branched hydrocarbon group having 1 to 12 carbon atoms and optionally one or more heteroatoms;
a saturated or unsaturated, monocyclic hydrocarbon group having 3 to 8 carbon atoms and optionally one or more heteroatoms; or
a monocyclic aryl or heteroaryl group;
or else $R^2$ and $R^3$ together form a —$(CH_2)_n$— group where n is an integer ranging from 1 to 4;
$R^4$ is a hydrogen atom, a saturated or unsaturated, straight-chain or branched hydrocarbon group having 2 to 8 carbon atoms, or a monocyclic aromatic group; whilst
$R^5$ is a hydrogen atom or saturated or unsaturated, straight-chain or branched hydrocarbon group having 1 to 12 carbon atoms.

Therefore, depending on the meaning of $R^2$ and $R^3$, the compound of the invention may meet:
* either the particular formula (I-a) below:

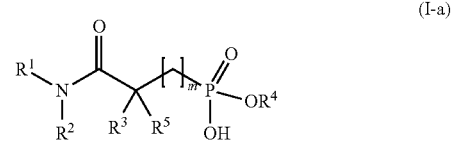

where:
m, $R^1$, $R^4$ and $R^5$ are such as previously defined;
$R^2$ is a saturated or unsaturated, straight-chain or branched hydrocarbon group having 6 to 12 carbon atoms; whilst R³ is:
a hydrogen atom;
a saturated or unsaturated, straight-chain or branched hydrocarbon group having 1 to 12 carbon atoms and optionally one or more heteroatoms;
a saturated or unsaturated, monocyclic hydrocarbon group having 3 to 8 carbon atoms and optionally one or more heteroatoms; or
a monocyclic aryl or heteroaryl group;
* or the particular formula (I-b) below:

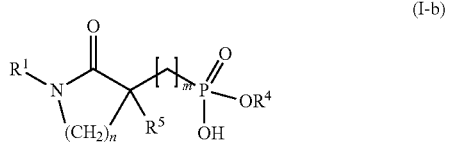

(I-b)

where m, n, $R^1$, $R^4$ and $R^5$ are such as previously defined.

According to the invention, by <<saturated or unsaturated, straight-chain or branched hydrocarbon group having 6 to 12 carbon atoms>>, is meant any straight-chain or branched alkyl, alkenyl or alkynyl group having 6, 7, 8, 9, 10, 11 or 12 carbon atoms.

Similarly, by <<saturated or unsaturated, straight-chain or branched hydrocarbon group having 2 to 8 carbon atoms>> is meant any straight-chain or branched alkyl, alkenyl or alkynyl group having 2, 3, 4, 5, 6, 7 or 8 carbon atoms.

By <<saturated or unsaturated, straight-chain or branched hydrocarbon group having 1 to 12 carbon atoms and optionally one or more heteroatoms>> is meant any group formed of a straight or branched hydrocarbon chain having 1, 2, 3, 4, 5, 6, 7, 8, 9, 10, 11 or 12 carbon atoms whose chain may be saturated or on the contrary may comprise one or more double or triple bonds and whose chain may be interrupted by one or more heteroatoms or substituted by one or more heteroatoms or by one or more substituents comprising a heteroatom.

In this respect, it is specified that by <<heteroatom>> is meant any atom other than carbon or hydrogen, this atom typically being a nitrogen, oxygen or sulphur atom.

Also, by <<saturated or unsaturated, monocyclic hydrocarbon group having 3 to 8 carbon atoms and optionally one or more heteroatoms>> is meant any cyclic hydrocarbon group which only comprises a single ring and the ring comprises 3, 4, 5, 6, 7 or 8 carbon atoms. This ring may be saturated, or on the contrary it may have one or more double or triple bonds, and may comprise one or more heteroatoms, or it may be substituted by one or more heteroatoms or by one or more substituents comprising a heteroatom, this or these heteroatoms typically being N, O or S. Therefore this group in particular may be a cycloalkyl, cycloalkenyl or cycloalkynyl group (e.g. a cyclopropane, cyclopentane, cyclohexane, cyclopropenyl, cyclopentenyl or cyclohexenyl group), a saturated heterocyclic group (e.g. a tetrahydrofuryl, tetrahydrothiophenyl, pyrrolidinyl or piperidinyl group), an unsaturated heterocyclic group but not aromatic (e.g. pyrrolinyl or pyridinyl), an aromatic group or a heteroaromatic group.

In this respect, it is pointed out that by <<aromatic group>> is meant any group of which the ring meets Hückel's rule of aromaticity and therefore has a number of delocalised electrons π of 4n+2 (e.g. a phenyl or benzyl group), whilst by <<heteroaromatic group>> is meant any aromatic group such as just defined but whose ring comprises one or more heteroatoms, this or these heteroatoms typically being selected from among nitrogen, oxygen and sulphur atoms (e.g. a furanyl, thiophenyl or pyrrolyl group).

Finally, the —$(CH_2)_n$— group in which n is an integer from 1 to 4, may be a methylene, ethylene, propylene or butylene group.

According to the invention, in the particular formula (I-a) above $R^1$ and $R^2$, which may be the same or different, are advantageously a straight-chain or branched alkyl group having 6 to 12 carbon atoms.

More preferably $R^1$ and $R^2$ are the same and are both a branched alkyl group having 8 to 10 carbon atoms, the 2-ethylhexyl group being most particularly preferred.

Also, in the above particular formula (I-a):
m preferably equals 0;
$R^3$ is advantageously a hydrogen atom, a straight-chain or branched alkyl group having 1 to 12 carbon atoms, or a monocyclic aryl group, preferably phenyl or ortho-, meta- or para-tolyl; whilst
$R^5$ is preferably a hydrogen atom.

Further preferably, $R^3$ is a hydrogen atom, a methyl, n-octyl or phenyl group.

Finally, in the above particular formula (I-a), $R^4$ is preferably a straight-chain or branched alkyl group having 2 to 8 carbons atoms and better still 2 to 4 carbon atoms such as an ethyl, n-propyl, isopropyl, n-butyl, sec-butyl, isobutyl or tert-butyl group, the ethyl and n-butyl groups being most particularly preferred.

Compounds of the above particular formula (I-a) which have these characteristics are in particular:
Ethyl 1-(N,N-diethylhexylcarbamoyl)benzylphosphonate, which meets above particular formula (I-a) wherein m equals 0, $R^1$ and $R^2$ are both a 2-ethyl-hexyl group, $R^3$ is a phenyl group, $R^4$ is an ethyl group whilst $R^5$ is a hydrogen atom;
Ethyl 1-(N,N-diethylhexylcarbamoyl)ethylphosphonate which meets the above particular formula (I-a) wherein m equals 0, $R^1$ and $R^2$ are both a 2-ethylhexyl group, $R^3$ is a methyl group, $R^4$ is an ethyl group whilst $R^5$ is a hydrogen atom;
Ethyl 1-(N,N-diethylhexylcarbamoyl)nonylphosphonate, which meets the above particular formula (I-a) wherein m equals 0, $R^1$ and $R^2$ are both a 2-ethyl-hexyl group, $R^3$ is an n-octyl group, $R^4$ is an ethyl group whilst $R^5$ is a hydrogen atom;
Butyl 1-(N,N-diethylhexylcarbamoyl)nonylphosphonate which meets the above particular formula (I-a) wherein m equals 0, $R^1$ and $R^2$ are both a 2-ethyl-hexyl group, $R^3$ is an n-octyl group, $R^4$ is an n-butyl group whilst $R^5$ is a hydrogen atom; and
Butyl 1-(N,N-dioctylcarbamoyl)nonylphosphonate which meets the above particular formula (I-a) wherein m equals 0, $R^1$, $R^2$ and $R^3$ are all an n-octyl group, $R^4$ is an n-butyl group whilst $R^5$ is a hydrogen atom.

Amongst these compounds particular preference is given to ethyl 1-(N,N-diethylhexylcarbamoyl)nonylphosphonate and butyl 1-(N,N-diethylhexylcarbamoyl)-nonylphosphonate.

In the particular family (I-b) given above, $R^1$ is advantageously a straight-chain or branched alkyl group having 6 to 12 carbon atoms.

Also, in this particular formula:
m preferably equals 0;
$R^4$ is preferably a straight-chain or branched alkyl group having 2 to 8 carbon atoms, and better still 2 to 4 carbon atoms, whilst
$R^5$ is preferably a hydrogen atom.

A compound of above particular formula (I-b) which has these characteristics is in particular ethyl (N-dodecylpyrrolidone)-1-phosphonate which meets the particular formula (I-b) wherein $R^1$ is an n-dodecyl group, $R^2$ and $R^3$ together form an ethylene group ($—CH_2—CH_2—$), $R^4$ is an ethyl group whilst $R^5$ is a hydrogen atom.

The compounds of the invention may be obtained in particular using the methods described in the examples below and in appended FIGS. 1 to 3. The compounds of the invention exhibit particularly high affinity and selectivity for uranium(VI).

In particular, the compounds of the invention are capable of extracting uranium(VI) with high efficacy from an aqueous solution of phosphoric acid and in particular from an aqueous solution containing 0.01 to 9 mol/L of phosphoric acid.

Therefore a further subject of the invention is the use of a compound such as previously defined as a ligand of uranium(VI), and in particular for the extraction of uranium (VI) from an aqueous solution of phosphoric acid, this aqueous solution preferably containing 0.01 to 9 mol/L phosphoric acid.

Said aqueous solution in particular may be a solution resulting from digestion of a natural phosphate with sulphuric acid.

The compounds of the invention can therefore be given notable use in a method allowing the recovery of uranium contained in an aqueous solution of phosphoric acid derived from the digestion of a natural phosphate with sulphuric acid, this method comprising:

a) extracting the uranium, in oxidation state VI, from this aqueous solution by contacting this solution with an organic phase comprising a compound such as previously defined, followed by separation of said aqueous solution and said organic phase;

b) washing the organic phase obtained at the end of step a) which is performed for example using water, an acid aqueous solution, e.g. an aqueous solution of sulphuric acid or an aqueous solution of ammonium oxalate;

c) stripping of uranium(VI) contained in the organic phase obtained at the end of step b) by contacting this organic phase with an aqueous solution comprising a carbonate or a mixture of carbonates, e.g. an ammonium or sodium carbonate, then separating said organic phase and said aqueous solution; and optionally:

d) acidifying the organic phase obtained at the end of step c) by contacting this organic phase with an acid aqueous solution, e.g. an aqueous solution of sulphuric acid or an aqueous solution of phosphoric acid.

In this method, the compound is advantageously used in solution, at a concentration of 0.01 to 1 mol/L, in an organic diluent, this diluent preferably being of aliphatic type such as n-dodecane, hydrogenated tetrapropylene or kerosene, for example the one marketed by TOTAL under the trade name Isane IP-185.

The aqueous solution of phosphoric acid used at step a) preferably comprises 0.01 to 9 mol/L of phosphoric acid, whilst the aqueous solution comprising the carbonate used at step c) preferably comprises 0.1 to 1.5 mol/L of carbonate(s).

In addition, this method allows strong concentrating of uranium(VI), i.e. obtaining at the end of step c) an aqueous solution having a uranium(VI) concentration higher than that contained in the aqueous solution of phosphoric acid used at step a). For example, this can be obtained through the choice of a volume ratio between the organic phase and the aqueous solution of phosphoric acid that is lower than 1 at step a), and a volume ratio between the organic phase and the aqueous solution comprising the carbonate(s) that is higher than 1 at step c). This allows to cause an increase in the concentration of uranium(VI) in the organic phase at step a) and in the aqueous phase at step c).

Other characteristics and advantages of the invention will become better apparent on reading the remainder of the description below which relates to examples of synthesis of compounds conforming to the invention and examples demonstrating the properties thereof.

Evidently, these examples are solely given to illustrate the subject of the invention and under no circumstances do they amount to any limitation of this subject.

DETAILED DESCRIPTION OF PARTICULAR EMBODIMENTS

EXAMPLE I

Synthesis Of Compounds Of The Invention

I.1—Synthesis of Compounds of Particular Formula (I-a)

Figure 1:
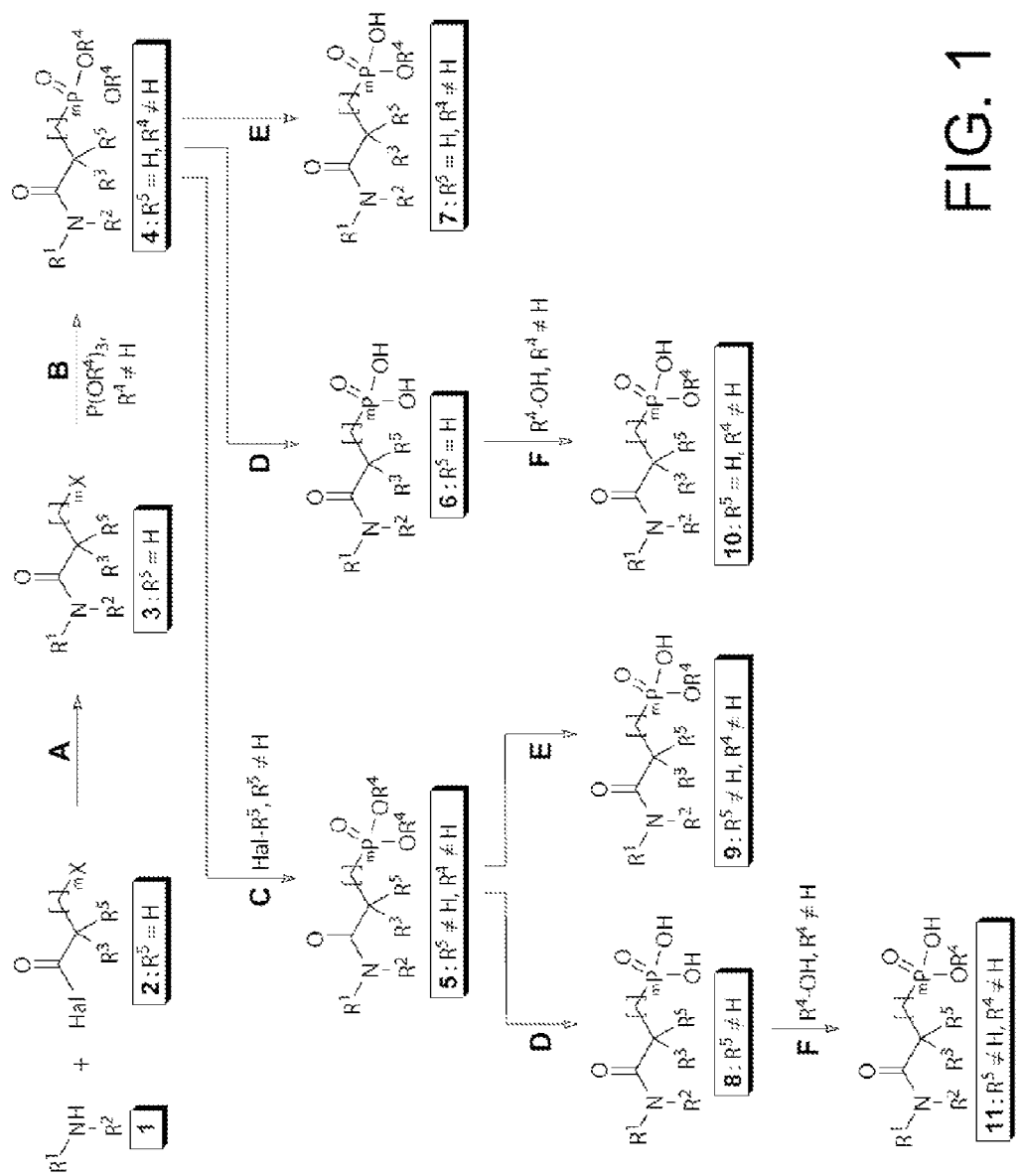
FIG. 1 illustrates the steps of methods for synthesising compounds of the invention which meet particular formula (I-a).

The compounds meeting the above particular formula (I-a), wherein m and $R^1$ to $R^5$ have the same meaning as previously, can be synthesised by following the reaction scheme illustrated in FIG. 1.

As can be seen in this Figure, this synthesis at a first step denoted A consists of causing an amine denoted 1 to react with an acid halide (e.g. a chloride or bromide) denoted 2, which is functionalised at α, at β or at γ (depending on the value of m in the compound which it is desired to synthesise) by a leaving group X (e.g. a chlorine or bromine atom) to obtain compound 3 in which $R^5$ is a hydrogen atom.

For this purpose, potassium carbonate (2 eq.) is added under agitation to a 0.7 mol/l solution of the amine in dichloromethane. The suspension thus obtained is cooled to 0° C. and the acid halide is added dropwise thereto (1.5 eq.). The mixture is left to return to ambient temperature. Once the amine is consumed (verified by thin layer chromatography (TLC) using ethyl acetate as eluent and ninhydrin for detection), 4 equivalents of water are added dropwise to the mixture, producing effervescence. When effervescence stops an amount of water is added to this mixture that is equal to one half of the volume of dichloromethane used to dissolve the amine. The mixture is left under agitation for 15 minutes. The aqueous and organic phases are then separated and the organic phase dried over $Na_2SO_4$, filtered and concentrated. Compound 3 thus obtained is generally sufficiently pure so that it can be used as such.

At a second step denoted B in FIG. 1, compound 3 is subjected to an Arbusov reaction to obtain compound 4 in which $R^4$ differs from a hydrogen atom whilst $R^5$ is a hydrogen atom.

This Arbusov reaction is performed by bringing a mixture composed of compound 3 and a phosphite $P(OR^4)_3$ wherein $R^4$ differs from a hydrogen atom (1.2 to 10 eq. as applicable) to 160° C. under reflux for 3 to 72 hours as applicable. Once compound 3 is consumed (verified by TLC using dichloromethane as eluent and UVs or phosphomolybdic acid for detection), the excess phosphite is distilled under reduced pressure. Depending on different cases, compound 4 can be used as such at the following step or on the contrary will require prior purification in which case this purification is performed by column chromatography with a cyclohexane/ethyl acetate elution gradient: from 100:0 to 60:40, v/v.

Resulting compound 4 is then subjected:
either to a C-alkylation step, denoted C in FIG. 1, through the action of a strong base (e.g. sodium hydride) and a halide Hal-$R^5$ in which $R^5$ differs from a hydrogen atom, to alkylate this compound at a of the amide group and obtain compound 5 wherein $R^4$ and $R^5$ both differ from a hydrogen atom;
or to a hydrolysis step, denoted D in FIG. 1, through the action of a halide (e.g. a bromide) of trimethylsilane, to obtain compound 6 in which $R^4$ and $R^5$ are both hydrogen atoms;
or to a monosaponification step, denoted E in FIG. 1, through the action of a strong base (for example sodium hydroxide or potash) to obtain compound 7 in which $R^4$ differs from a hydrogen atom whilst $R^5$ is a hydrogen atom.

Step C (C-alkylation) is conducted by adding dropwise and under agitation a solution of compound 4 (previously vacuum dried for 2.5 hours at 80° C.) in tetrahydrofuran (THF—1 eq.—1 mol/L) to a suspension of sodium hydride (2 eq.—previously washed in pentane) in anhydrous THF (2 mol/L). The mixture is left under agitation for 1 hour at ambient temperature after which the solution is cooled to 0° C. and a solution of the halide Hal-$R^5$ (1.5 eq.) is added dropwise. This mixture is left to return to ambient temperature and then left under agitation overnight, after which the reaction mixture is acidified to pH 1 using a 1 mol/L aqueous solution of hydrochloric acid, and extracted with dichloromethane. The aqueous and organic phases are separated and the organic phase dried over $Na_2SO_4$, filtered and concentrated. The excess halide is removed by vacuum distillation.

Step D (hydrolysis) is conducted by adding the trimethylsilane bromide (6 eq.) dropwise and under agitation to a 0.25 mol/L solution of compound 4 in dichloromethane, and the mixture is left under agitation overnight. Methanol is then added to the mixture and it is again left under agitation for 2 hours. It is concentrated. The reaction medium is then diluted in dichloromethane, washed once with water and once with 1 mol/L hydrochloric acid. The aqueous and organic phases are separated and the organic phase dried over $Na_2SO_4$, filtered and concentrated.

Step E (monosaponification) is conducted by adding a solution of the strong base (6 to 8 eq.) to a 0.4 mol/L solution of compound 4 in ethanol. The mixture is refluxed for 2.5 to 12 hours depending on cases. After cooling, the mixture is acidified to pH 1 using a 1 mol/L aqueous solution of hydrochloric acid and then extracted twice with dichloromethane. The aqueous and organic phases are separated and the organic phase dried over $Na_2SO_4$, filtered and concentrated.

Compound 5 obtained at step C is then subjected either to step D described above to obtain the compound denoted 8 in FIG. 1 and wherein $R^4$ is a hydrogen atom whilst $R^5$ differs from a hydrogen atom, or to step E described above to obtain the compound denoted 9 in this Figure and wherein $R^4$ and $R^5$ both differ from a hydrogen atom.

It is possible to obtain compounds of particular formula (I-a) wherein $R^4$ represents a group different from group $R^4$ contained in compound 4 (and which is contributed by the phosphite $P(OR^4)_3$ at step B) by subjecting either compound 6 or compound 8 (depending on whether $R^5$ must or must not represent a hydrogen atom) to an additional O-alkylation step, denoted F in FIG. 1, through the action of an alcohol $R^4$—OH wherein $R^4$ differs from a hydrogen atom, to obtain either compound 10 wherein $R^4$ differs from a hydrogen atom whilst $R^5$ is a hydrogen atom, or compound 11 wherein $R^4$ and $R^5$ both differ from a hydrogen atom.

In this manner the following compounds are synthesised:

I.1.1—1-(N,N-diethylhexylcarbamoyl)methylphosphonic acid

The title compound, denoted ADEHCMP, which meets particular formula (I-a) wherein m=0, $R^1$=$R^2$=2-ethylhexyl and $R^3$=$R^4$=$R^5$=H, is synthesised by performing steps A, B and D of the reaction scheme shown in FIG. 1.

Step A is performed using 2,2'-diethylhexylamine and chloroacetyl chloride and leads to 2-chloro-N,N-diethylhexylacetamide (Yield: 97%) for which the $^1$H and $^{13}$C NMR characterisations are given below:

$^1$H NMR (400 MHz, $CDCl_3$) δ (ppm): 0.85-0.91 (m, 12H, $CH_3$); 1.23-1.33 (m, 16H, $CH_2$); 1.55-1.60 (m, 1H, CH—$CH_2$—N); 1.67-1.73 (m, 1H, CH—$CH_2$—N); 3.18 (d, 2H, J=7.5 Hz, $CH_2$—N); 3.22-3.32 (m, 2H, $CH_2$—N); 4.09 (s, 2H, $CH_2$—Cl).

$^{13}$C NMR (100 MHz, $CDCl_3$) δ (ppm): 10.7; 11.0; 14.1 ($CH_3$); 23.1; 23.9; 24.0; 28.7; 28.9; 30.4; 30.6 ($CH_2$); 36.8; 38.5 (CH); 41.6 ($CH_2$—Cl); 48.8 ($CH_2$—N); 51.7 ($CH_2$—N); 167.1 (C=O).

Step B is conducted using triethylphosphite (1.2 eq. per 1 eq. of 2-chloro-N,N-diethylhexylacétamide—reflux for 3 hours) and leads to diethyl 1-(N,N-diethylhexylcarbamoyl)methylphosphonate (Yield: quantitative) for which the characterisations by $^1$H, $^{13}$C and $^{31}$P NMR are given below:

¹H NMR (400 MHz, CDCl₃) δ (ppm): 0.81-0.86 (m, 12H, CH₃); 1.21-1.32 (m, 22H, CH₂, O—CH₂—CH₃); 1.51-1.57 (m, 1H, CH—CH₂—N); 1.64-1.71 (m, 1H, CH—CH₂—N); 3.02 (d, 2H, J=22.0 Hz, CO—CH₂—P); 3.21-3.27 (m, 4H, CH₂—N); 4.08-4.16 (m, 4H, O—CH₂—CH₃).

¹³C NMR (100 MHz, CDCl₃) δ (ppm): 10.6; 11.0; 14.1; 14.2 (CH₃); 16.3; 16.4 (O—CH₂—CH₃); 23.1; 23.2; 23.5; 23.9; 28.8; 28.9; 30.4; 30.6 (CH₂); 33.1; 34.5 (d, J=134.0 Hz, CH₂—P); 37.0; 38.6 (CH); 48.9; 52.3 (CH₂—N); 62.5 (d, J=6.5 Hz, O—CH₂—CH₃); 165.2 (d, J=6.0 Hz, C=O).

³¹P NMR (160 MHz, CDCl₃) δ (ppm): 21.8.

Step D leads to the title compound (Yield: quantitative) for which the ¹H, ¹³C, ³¹P NMR characterisations are given below:

¹H NMR (400 MHz, CDCl₃) δ (ppm): 0.86-0.93 (m, 12H, CH₃); 1.22-1.37 (m, 16H, CH₂); 1.59-1.65 (m, 1H, CH—CH₂—N); 1.70-1.76 (m, 1H, CH—CH₂—N); 3.07 (d, 2H; J=21.5 Hz, CO—CH₂—P); 3.21-3.42 (m, 4H, CH₂—N); 9.56 (ls, 2H, OH).

¹³C NMR (100 MHz, CDCl₃) δ (ppm): 10.5; 10.8; 14.0; 14.1 (CH₃); 23.0; 23.5; 23.7; 28.5; 28.7 (CH₂); 26.8 (CH₂—CH₂—N); 27.1; 27.3 (CH₂); 28.7 (CH₂—CH₂—N); 29.5; 29.7; 29.1; 32.0 (CH₂); 32.4; 33.8 (d, J=131.0 Hz, CH₂—P); 48.2; 50.1 (CH₂—N); 168.5 (d, J=5.5 Hz, C=O).

³¹P NMR (160 MHz, CDCl₃) δ (ppm): 21.0.

I.1.2—1-(N,N-diethylhexylcarbamoyl)benzylphosphonic acid

The title compound, denoted ADEHMCBP, which meets particular formula (I-a) wherein m=0, R¹=R²=2-ethylhexyl, R³=phenyl and R⁴=R⁵=H, is synthesised by performing steps A, B and D of the reaction scheme shown in FIG. 1.

Step A is conducted starting from 2,2'-diethylhexylamine and α-chlorophenylacetyl chloride and leads to 2-chloro-N,N-bis(2-ethylhexyl)-2-phenyl-acetamide (Yield: 96%) for which the characterisations by ¹H and ¹³C NMR are given below:

¹H NMR (400 MHz, CDCl₃) δ (ppm): 0.79-0.91 (m, 12H, CH₃); 1.09-1.37 (m, 16H, CH₂); 1.56-1.64 (m, 1H, CH—CH₂—N); 1.65-1.73 (m, 1H, CH—CH₂—N); 3.05-3.22 (m, 3H, CH₂—N); 3.38-3.47 (m, 1H, CH₂—N); 5.66 (s, 1H, CO—CH(Ph)-Cl); 7.29-7.36 (m, 3H, $CH_{Ar}$); 7.47-7.49 (m 2H, $CH_{Ar}$).

¹³C NMR (100 MHz, CDCl₃) δ (ppm): 10.5; 10.7; 10.8; 10.9 (CH₃—CH₂—CH); 14.1 (CH₃); 23.0; 23.7; 23.8 (CH₂); 28.6; 28.7; 28.8; 28.9 (CH₂); 30.4; 30.5; 30.6 (CH₂); 36.9; 37.0; 39.1; 39.2 (CH); 50.1; 50.2; 50.3 (CH₂—N); 51.8; 51.9 (CH₂—N); 57.6; 57.7 (CO—CH(Ph)-Cl); 128.3; 128.8 ($CH_{Ar}$); 129.0; 136.6 ($C_{Ar}$); 167.7 (C=O).

Step B is performed using triethylphosphite (10 eq. per 1 eq. of 2-chloro-N,N-bis(2-ethylhexyl)-2-phenylacetamide—reflux for 72 hours) and leads to 1-(N,N-diethylhexylcarbamoyl)diethyl benzylphosphonate (Yield: 47%) for which the ¹H, ¹³C and ³¹P characterisations are given below:

¹H NMR (400 MHz, CDCl₃) δ (ppm): 0.80-0.92 (m, 12H, CH₃); 1.08-1.35 (m, 22H, CH₂, O—CH₂—CH₃); 1.54-1.75 (m, 2H, CH—CH₂—N); 2.98-3.19 (m, 3H, CH₂—N); 3.41-3.52 (m, 1H, CH₂—N); 3.97-4.07 (m, 2H, O—CH₂—CH₃); 4.09-4.23 (m, 2H, O—CH₂—CH₃); 4.48 (dd, 1H, J=23.0 Hz, 3.5 Hz, CO—CH(Ph)-P); 7.25-7.35 (m, 3H, $CH_{Ar}$); 7.48 (m, 2H, $CH_{Ar}$).

¹³C NMR (100 MHz, CDCl₃) δ (ppm): 10.4; 10.6; 10.7; 10.9; 14.0; 14.1 (CH₃); 16.3; 16.4 (O—CH₂—CH₃); 22.9; 23.0; 23.1; 23.2; 23.5; 23.6; 23.7; 23.8; 28.6; 28.8; 30.3; 30.6 (CH₂); 36.9; 37.0; 37.1; 38.8; 38.9; 39.0 (CH); 49.2; 49.4; 49.6; 49.9 (CH₂—N); 49.8; 51.3 (d, J=146 Hz, CH(Ph)-P); 51.9; 52.3 (CH₂—N); 62.7 (d, J=7.0 Hz, O—CH₂—CH₃); 63.0 (d, J=6.0 Hz, O—CH₂—CH₃); 127.6 ($CH_{Ar}$); 128.5 ($CH_{Ar}$); 129.5; 129.6 ($CH_{Ar}$); 132.1; 132.2 ($C_{Ar}$); 167.7 (dd, J=6.0 Hz, J=3.5 Hz, C=O).

³¹P NMR (160 MHz, CDCl₃) δ (ppm): 20.6.

Step D leads to the title compound (Yield: 89%) for which the ¹H, ¹³C and ³¹P NMR characterisations are given below:

¹H NMR (400 MHz, CDCl₃) δ (ppm): 0.77-0.93 (m, 12H, CH₃); 1.05-1.44 (m, 16H, CH₂); 1.53-1.61 (m, 1H, CH—CH₂—N); 1.65-1.75 (m, 1H, CH—CH₂—N); 2.92-3.06 (m, 2H, CH₂—N); 3.15-3.21 (m, 1H, CH₂—N); 3.56-3.65 (m, 1H, CH₂—N); 4.42-4.49 (dd, 1H, J=23.0 Hz, 7.5 Hz, C(O)—CH(Ph)P(O)); 7.24-7.40 (m, 5H, $CH_{Ar}$); 10.55 (ls, 2H, OH).

¹³C NMR (100 MHz, CDCl₃) δ (ppm): 10.2; 10.4; 10.5; 10.6; 10.7; 11.0; 14.1; 14.2 (CH₃); 23.0; 23.1; 23.2; 23.5; 23.6; 23.7; 23.8; 28.7; 28.8; 28.9; 30.3; 30.4; 30.5; 30.6 (CH₂); 36.8; 36.9; 37.0; 37.1; 38.4; 38.5; 38.7; 38.8 (CH); 48.7; 50.0 (d, J=132 Hz; C(O)CH(Ph)P(O)); 49.4; 49.7; 50.3; 50.5; 52.0; 52.1; 52.2; 52.4 (CH₂—N); 127.6; 128.8; 129.0; 129.1 ($CH_{Ar}$); 132.2; 132.3 ($C_{Ar}$); 163.8 ($CH_{Ar}$); 170.6 (C=O).

³¹P NMR (160 MHz, CDCl₃) δ (ppm): 22.5.

I.1.3—Ethyl 1-(N,N-diethylhexylcarbamoyl)methylphosphonate

The title compound, denoted DEHCEPE, which meets particular formula (I-a) wherein m=0, R¹=R²=2-ethylhexyl, R³=methyl, R⁴=ethyl and R⁵=H, is synthesised by performing steps A, B and E of the reaction scheme shown in FIG. 1.

Step A is conducted starting with 2,2'-diethylhexylamine and 2-bromopropionyl chloride and leads to 2-bromo-N,N-bis(2-ethylhexyl)propanamide (Yield: 98%) for which the ¹H and ¹³C NMR characterisations are the following:

¹H NMR (400 MHz, CDCl₃) δ (ppm): 0.83-0.89 (m, 12H, CH₃); 1.14-1.35 (m, 16H, CH₂); 1.48-1.55 (m, 1H, CH—CH₂—N); 1.67-1.75 (m, 1H, CH—CH₂—N); 1.78 (d, 3H, J=6.5 Hz, COCH(Br)CH₃); 2.68-2.76 (m, 1H, CH₂—N); 2.68-2.76 (dd, 1H, J=15.0 Hz, 7.0 Hz, CH₂—N); 3.30-2.38 (m, 1H, CH₂—N); 3.73-3.82 (m, 1H, CH₂—N); 4.55 (q, 1H, J=6.5 Hz, COCH(Br)CH₃).

¹³C NMR (100 MHz, CDCl₃) δ (ppm): 10.5; 10.8; 11.0 (CH₃—CH₂—CH); 14.0; 14.1 (CH₃); 21.6 (COCH(Br)CH₃); 23.0; 23.5; 23.8; 24.0 (CH₂); 28.7; 28.8 (CH₂); 30.2; 30.5; 30.6; 30.7 (CH₂); 37.0; 37.1 (CH); 38.9 (COCH(Br)CH₃); 39.2; 39.3 (CH); 49.5; 49.6; 49.7; 49.8 (CH₂—N); 51.7; 51.8; 51.9; 60.0 (CH₂—N); 57.6; 57.7 (CO—CH(Ph)-Br); 128.3; 128.8 ($CH_{Ar}$); 129.0; 136.6 ($C_{Ar}$); 167.7 (C=O).

Step B is performed using triethylphosphite (10 eq. per 1 eq. of 2-bromo-N,N-bis(2-ethylhexyl)propanamide—reflux for 72 hours) and leads to diethyl 1-(N,N-diethylhexylcarbamoyl)ethylphosphonate (Yield: 54%), the ¹H, ¹³C and ³¹P NMR characterisations thereof being as follows:

¹H NMR (400 MHz, CDCl₃) δ (ppm): 0.80-0.92 (m, 12H, CH₃); 1.13-1.35 (m, 22H, CH₂, O—CH₂—CH₃); 1.42 (dd, 3H, J=18.5 Hz, J=7.0 Hz, CH₃—CH(CO)—P); 1.48-1.56 (m, 1H, CH—CH₂—N); 1.68-1.76 (m, 1H, CH—CH₂—N); 2.76-2.83 (m, 1H, CH₂—N); 2.95-3.03 (m, 1H, CH₂—N); 3.28 (dqd, 1H, J=21.5 Hz, J=7.0 Hz, J=2.0 Hz, CH₃—CH(CO)—P); 3.41-3.52 (m, 1H, CH₂—N); 3.65-3.78 (m, 1H, CH₂—N); 4.05-4.17 (m, 4H, O—CH₂—CH₃).

¹³C NMR (100 MHz, CDCl₃) δ (ppm): 10.4; 10.6; 10.9; 11.0 (CH₃); 12.9 (CH₃—CH(CO)—P); 14.0; 14.1 (CH₃); 16.4; 16.5 (O—CH₂—CH₃); 23.0; 23.1; 23.2; 23.6; 23.7; 23.9; 28.6; 28.7; 28.9; 30.2; 30.3; 30.4; 30.5; 30.6 (CH₂);

35.5; 36.8 (d, J=134.0 Hz, CH₃—CH(CO)—P); 37.1; 37.2; 38.8; 39.0 (CH—CH₂—N); 49.3 (d, J=8.5 Hz, CH₂—N); 50.1 (d, J=5.5 Hz, CH₂—N); 51.7 (d, J=7.5 Hz, CH₂—N); 52.4 (d, J=9.5 Hz, CH₂—N); 62.2 (d, J=6.5 Hz, O—CH₂—CH₃); 62.6 (d, J=5.5 Hz, O—CH₂—CH₃); 169.4 (d, J=4.5 Hz, C=O).

$^{31}$P NMR (160 MHz, CDCl₃) δ (ppm): 25.3.

Step E is performed using potash (4 eq. per 1 eq. of diethyl 1-(N,N-diethylhexylcarbamoyl)ethylphosphonate—reflux for 6 hours) and leads to the title compound (Yield: 97%) for which characterisations by $^1$H, $^{13}$C and $^{31}$P NMR are the following:

RMN $^1$H (400 MHz, CDCl₃) δ (ppm): 0.84-0.92 (m, 12H, CH₃); 1.20-1.33 (m, 19H, CH₂, O—CH₂—CH₃); 1.42 (dd, 3H, J=18.5 Hz, J=7.0 Hz, CH₃—CH(CO)—P); 1.53-1.60 (m, 1H, CH—CH₂—N); 1.68-1.78 (m, 1H, CH—CH₂—N); 2.95-3.00 (dd, 1H, J=13.5 Hz, J=6.5 Hz, CH₂—N); 3.04-3.10 (ddd, 1H, J=15.0 Hz, J=6.5 Hz, J=3.0 Hz, CH₂—N); 3.24-3.34 (dqd, 1H, J=21.5 Hz, J=7.0 Hz, J=2.0 Hz, CO—CH(CH₃)—P); 3.36-3.44 (m, 1H, CH₂—N); 3.51-3.63 (m, 1H, CH₂—N); 4.09-4.19 (m, 2H, O—CH₂—CH₃), 10.5 (ls, 1H, OH).

$^{13}$C NMR (100 MHz, CDCl₃) δ (ppm): 10.6; 10.7; 11.0; 11.0 (CH₃); 12.9 (d, J=6.0 Hz, CH₃—CH(CO)—P); 14.1; 14.2 (CH₃); 16.5 (d, J=6.0 Hz, O—CH₂—CH₃); 23.1; 23.2; 23.3; 23.6; 23.8; 23.9; 28.8; 29.0; 30.5; 30.6; 30.7 (CH₂); 35.0; 36.4 (d, J=136.5 Hz, CH₃—CH(CO)—P); 37.3; 38.9; 39.0; 39.1; 39.2 (CH—CH₂—N); 49.6; 49.7; 50.3; 50.4; 52.0; 52.1; 52.7; 52.8 (CH₂—N); 62.2 (d, J=6.5 Hz, O—CH₂—CH₃); 170.7 (d, J=4.5 Hz, C=O).

$^{31}$P NMR (160 MHz, CDCl₃) δ (ppm): 27.5.

I.1.4—Ethyl 1-(N,N-dihexylcarbamoyl)methylphosphonate

The title compound, denoted DHCMPE, which meets particular formula (I-a) wherein m=0, $R^1=R^2$=n-hexyl, $R^3=R^5$=H and $R^4$=ethyl, is synthesised by performing steps A, B and E of the reaction scheme shown in FIG. 1.

Step A is conducted using dihexylamine and chloroacetyl chloride and leads to 2-chloro-N,N-dihexylacetamide (Yield: 97%) for which the $^1$H and $^{13}$C NMR characterisations are the following:

$^1$H NMR (400 MHz, CDCl₃) δ (ppm): 0.75-0.79 (m, 6H, Hz, CH₃); 1.15-1.22 (m, 12H, CH₂); 1.40-1.51 (m, 4H, CH₂—CH₂—N); 3.13-3.22 (m, 4H, CH₂—N); 3.94 (s, 2H, CH₂—Cl).

$^{13}$C NMR (100 MHz, CDCl₃) δ (ppm): 13.8; 13.9 (CH₃); 22.4; 26.3, 26.4 (CH₂); 27.1; 28.9 (CH₂—CH₂—N); 31.3; 31.4 (CH₂); 41.2 (CH₂—Cl); 46.0; 48.1 (CH₂—N); 165.8 (C=O).

Step B is performed using triethylphosphite (1.2 eq. per 1 eq. of 2-chloro-N,N-dihexylacetamide—reflux for 3 hours) and leads to diethyl 1-(N,N-dihexyl-carbamoyl)methylphosphonate (Yield: quantitative) for which the $^1$H, $^{13}$C and $^{31}$P NMR characterisations are as follows:

$^1$H NMR (400 MHz, CDCl₃) δ (ppm): 0.84-0.90 (m, 6H, Hz, CH₃); 1.24-1.34 (m, 18H, CH₂, O—CH₂—CH₃); 1.48-1.78 (m, 4H, CH₂—CH₂—N); 3.00 (d, 2H, J=22.0 Hz, CO—CH₂—P); 3.28-3.33 (m, 4H, CH₂—N); 4.13-4.20 (m, 4H, O—CH₂—CH₃).

$^{13}$C NMR (100 MHz, CDCl₃) δ (ppm): 14.1; 14.2 (CH₃); 16.4; 16.5 (CH₃—CH₂—O); 22.7; 26.6; 26.7 (CH₂); 27.7; 29.1 (CH₂—CH₂—N); 31.7; 31.8 (CH₂); 32.9; 34.2 (d, J=134 Hz, CH₂—P); 46.4 (CH₂—N); 49.0 (CH₂—N); 62.7 (d, J=6.0 Hz, O—CH₂—CH₃); 164.4 (d, J$_{CP}$=5.5 Hz, C=O).

$^{31}$P NMR (160 MHz, CDCl₃) δ (ppm): 21.7.

Step E is performed using potash (4 eq. per 1 eq. of diethyl 1-(N,N-dihexylcarbamoyl)methylphosphonate—reflux for 2.5 hours) and leads to the title compound (Yield: 97%) for which the $^1$H, $^{13}$C and $^{31}$P NMR characterisations are the following:

$^1$H NMR (400 MHz, CDCl₃) δ (ppm): 0.77-0.82 (m, 6H, CH₃); 1.14-1.24 (m, 15H, CH₂, O—CH₂—CH₃); 1.40-1.51 (m, 4H, CH₂—CH₂—N); 2.95 (d, 2H, J=22.0 Hz, CO—CH₂—P); 3.20-3.26 (m, 4H, CH₂—N); 4.03-4.10 (m, 2H, O—CH₂—CH₃); 6.94 (ls, 1H, OH).

$^{13}$C NMR (100 MHz, CDCl₃) δ (ppm): 13.9; 14.0 (CH₃); 16.3 (d, J=6.5 Hz, CH₃—CH₂—O) 22.6; 26.5; 26.6 (CH₂; 27.4; 28.9 (CH₂—CH₂—N); 31.5; 31.6 (CH₂); 32.4; 33.7 (d, J=134 Hz, CH₂—P); 46.6; 49.0 (CH₂—N); 62.6; 62.7 (d, J=6.5 Hz, O—CH₂—CH₃); 164.8 (d, J$_{CP}$=5.5 Hz, C=O).

$^{31}$P NMR (160 MHz, CDCl₃) δ (ppm): 21.1.

I.1.5—Ethyl 1-(N,N-diethylhexylcarbamoyl)methylphosphonate

The title compound, denoted DEHCMPE, which meets particular formula (I-a) wherein m=0, $R^1=R^2$=2-ethylhexyl, $R^3=R^5$=H and $R^4$=ethyl, is synthesised by performing steps A, B and E of the reaction scheme shown in FIG. 1.

Steps A and B are identical to steps A and B described under item I.1.1 above.

Step E is conducted using potash (4 eq. per 1 eq. of diethyl 1-(N,N-diethylhexylcarbamoyl)methylphosphonate—reflux for 2.5 hours) and leads to the title compound (Yield: 97%) for which the $^1$H, $^{13}$C and $^{31}$P NMR characterisations are the following:

$^1$H NMR (400 MHz, CDCl₃) δ (ppm): 0.81-0.89 (m, 12H, CH₃); 1.17-1.33 (m, 19H, CH₂, O—CH₂—CH₃); 1.53-1.59 (m, 1H, CH—CH₂—N); 1.64-1.71 (m, 1H, CH—CH₂—N); 3.02 (d, 2H, J=22.0 Hz, CO—CH₂—P); 3.21-3.34 (m, 4H, CH₂—N); 4.08-4.16 (m, 2H, O—CH₂—CH₃); 10.3 (ls, 1H, OH).

$^{13}$C NMR (100 MHz, CDCl₃) δ (ppm): 10.7; 11.0; 14.2; 14.3 (CH₃); 16.5 (d, J=6.5 Hz, O—CH₂—CH₃); 23.1; 23.2; 23.7; 24.0; 28.8; 28.9; 30.5; 30.6 (CH₂); 32.5; 33.8 (d, J=134.0 Hz, CH₂—P); 37.2; 38.7 (CH); 48.6 (CH₂—N); 52.6 (CH₂—N); 62.1 (d, J=6.5 Hz, O—CH₂—CH₃); 165.1 (d, J=4.5 Hz, C=O).

$^{31}$P NMR (160 MHz, CDCl₃) δ (ppm): 21.8.

I.1.6—1-(N,N-diethylhexylcarbamoyl)-1-methylethylphosphonic acid

The title compound, denoted ADEHCEMP, which meets particular formula (I-a) wherein m=0, $R^1=R^2$=2-ethylhexyl, $R^3$=methyl, $R^4$=H and $R^5$=methyl, is synthesised by performing steps A, B, C and D of the reaction scheme shown in FIG. 1.

Steps A and B are identical to the steps described under item I.1.3 above.

Step C is conducted using iodomethane and leads to diethyl 1-(N,N-diethylhexylcarbamoyl)-1-methylethylphosphonate (Yield: 95%) for which the $^1$H, $^{13}$C and $^{31}$P NMR characterisations are as follows:

$^1$H NMR (400 MHz, CDCl₃) δ (ppm): 0.82-0.87 (m, 12H, CH₃); 1.19-1.30 (m, 22H, CH₂, O—CH₂—CH₃); 1.50 (d, 6H, J=17.0 Hz, C(O)—C(—P)—(CH₃)₂); 1.56-1.63 (m, 2H, CH—CH₂—N); 3.17-3.54 (multiplet, 4H, CH₂—N); 4.05-4.15 (m, 4H, O—CH₂—CH₃).

$^{13}$C NMR (100 MHz, CDCl₃) δ (ppm): 10.9-11.5 (multiplet); 14.1 (CH₃); 16.4; 16.5 (O—CH₂—CH₃); 23.0; 23.5

(CH$_2$); 23.6 (C(O)—C(—P)—(CH$_3$)$_2$); 23.8; 28.8-29.5 (multiplet); 30.5 (CH$_2$); 36.2; 37.6 (multiplet, CH); 45.4; 46.7 (d, J=137.0 Hz, C(O)—C(—P)—(CH$_3$)$_2$); 51.0 (multiplet, CH$_2$—N); 62.4; (O—CH$_2$—CH$_3$); 172.4 (C=O).

$^{31}$P NMR (160 MHz, CDCl$_3$) δ (ppm): 29.0.

Step D leads to the title compound (Yield: 95%) for which the $^1$H, $^{13}$C and $^{31}$P NMR characterisations are the following:

$^1$H NMR (400 MHz, CDCl$_3$) δ (ppm): 0.77-0.93 (m, 12H, CH$_3$); 1.05-1.44 (m, 16H, CH$_2$); 1.59 (d, 8H, J=17.0 Hz, CO—C(P)—(CH$_3$)$_2$, and CH—CH$_2$—N); 3.23-3.35 (multiplet, 4H, CH$_2$—N); 10.49 (ls, 2H, OH).

$^{13}$C NMR (100 MHz, CDCl$_3$) δ (ppm): 10.2; 10.4; 14.1; 14.2 (CH$_3$); 21.6 (CO—C(P)—(CH$_3$)$_2$); 22.6; 22.9; 23.0; 23.6; 23.8; 28.3; 28.8; 30.4; 30.5 (CH$_2$); 36.1; 37.5 (CH); 44.4; 45.8 (CO—C(P)—(CH$_3$)$_2$); 48.6; 51.5 (CH$_2$—N); 176.4 (C=O).

$^{31}$P NMR (160 MHz, CDCl$_3$) δ (ppm): 32.8.

I.1.7—Ethyl 1-(N,N-diethylhexylcarbamoyl)benzylphosphonate

The title compound, denoted DEHCBPE, which meets particular formula (I-a) wherein m=0, R$^1$=R$^2$=2-ethylhexyl, R$^3$=phenyl, R$^4$=ethyl and R$^5$=H, is synthesised by performing steps A, B and E of the reaction scheme shown in FIG. 1.

Steps A and B are identical to steps A and B described under item I.1.2 above.

Step E is conducted using potash (10 eq. per 1 eq. of diethyl 1-(N,N-diethylhexylcarbamoyl)benzylphosphonate—reflux for 24 hours) and leads to the title compound (Yield: 91%) for which the $^1$H, $^{13}$C and $^{31}$P NMR characterisations are as follows:

$^1$H NMR (400 MHz, CDCl$_3$) δ (ppm): 0.76-0.89 (m, 12H, CH$_3$); 1.06-1.32 (m, 19H, CH$_2$, O—CH$_2$—CH$_3$); 1.50-1.59 (m, 1H, CH—CH$_2$—N); 1.61-1.70 (m, 1H, CH—CH$_2$—N); 2.88-3.15 (m, 3H, CH$_2$—N); 3.24-3.54 (m, 1H, CH$_2$—N); 3.93-4.04 (m, 2H, O—CH$_2$—CH$_3$); 4.35 (dd, 1H, J=23.0 Hz, 5.0 Hz, CO—CH(Ph)-P); 7.20-7.40 (m, 5H, CH$_{Ar}$); 8.80 (s, 1H, OH).

$^{13}$C NMR (100 MHz, CDCl$_3$) δ (ppm): 10.3; 10.6; 11.0; 14.1 (CH$_3$); 16.4 (d, J=5.5 Hz, O—CH$_2$—CH$_3$); 22.9; 23.0; 23.5; 23.6; 23.7; 23.8; 23.9; 28.6; 28.7; 28.8; 30.3; 30.4 (CH$_2$); 36.8; 36.9; 37.1; 37.1; 38.5; 38.6; 38.7; 38.9 (CH); 48.4; 49.8 (d, J=139.0 Hz, CH(Ph)-P); 49.5; 50.2; (CH$_2$—N); 51.9; 52.3 (CH$_2$—N); 62.4 (d; J=7.0 Hz; O—CH$_2$—CH$_3$); 126.6 (CH$_{Ar}$); 127.7 (CH$_{Ar}$); 128.8; 129.2 (CH$_{Ar}$); 131.5; 135.6 (C$_{Ar}$); 169.2 (C=O).

$^{31}$P NMR (160 MHz, CDCl$_3$) δ (ppm): 22.0.

I.1.8—Ethyl 1-(N,N-diethylhexylcarbamoyl)nonylphosphonate

The title compound, denoted DEHCNPE, which meets particular formula (I-a) wherein m=0, R$^1$=R$^2$=2-ethylhexyl, R$^3$=H, R$^4$=ethyl and R$^5$=n-octyl, is synthesised by performing steps A, B, C and E of the reaction scheme shown in FIG. 1.

Steps A and B are the same as steps A and B described under item I.1.1 above.

Step C is conducted using octyl iodide and leads to diethyl 1-(N,N-diethylhexylcarbamoyl)nonylphosphonate (Yield: 99%) for which the $^1$H, $^{13}$C and $^{31}$P NMR characterisations are the following:

$^1$H NMR (400 MHz, CDCl$_3$) δ (ppm): 0.80-0.88 (m, 15H, CH$_3$); 1.13-1.40 (m, 34H, CH$_2$, O—CH$_2$—CH$_3$); 1.55-1.61 (m, 1H, CH—CH$_2$—N); 1.66-1.74 (m, 1H, CH—CH$_2$—N); 1.76-1.84 (m, 1H, C$_7$H$_{15}$—CH$_2$—CH—(CO)P); 2.00-2.14 (C$_7$H$_{15}$—CH$_2$—CH—(CO)P); 2.82-2.84 (m, 1H, CH$_2$—N); 2.96-3.04 (m, 1H, CH$_2$—N); 3.28 (ddq, 1H, J=22.0 Hz, J=10.5 Hz, J=3.0 Hz, CO—CH(Oct)-P); 3.39-3.51 (m, 1H, CH$_2$—N); 3.58-3.74 (m, 1H, CH$_2$—N); 4.04-4.18 (m, 4H, O—CH$_2$—CH$_3$).

$^{13}$C NMR (100 MHz, CDCl$_3$) δ (ppm): 10.3; 10.6; 10.8; 10.9; 14.0; 14.1 (CH$_3$); 16.4 (CH$_3$—CH$_2$—O); 22.6; 23.0; 23.1; 23.2; 23.6; 23.8; 26.9 (CH$_2$); 28.1 (C$_7$H$_{15}$—CH$_2$—CH—(CO)P); 28.2; 28.6; 28.8; 28.9; 29.0; 29.2; 29.4; 29.7; 29.8; 30.3; 30.4; 30.5; 30.7; 31.8 (CH$_2$); 37.1; 37.2; 37.3; 37.4; 39.1; 39.2; 39.3; 39.4 (CH—CH$_2$—N); 41.8; 43.1 (d, J=132.0 Hz, CO—CH(Oct)-P); 50.0 (d, J=25.0 Hz, CH$_2$—N); 50.8 (d, J=25.0 Hz, CH$_2$—N); 51.9 (d, J=11.0 Hz, CH$_2$—N); 52.5 (d, J=11.0 Hz, CH$_2$—N); 62.2 (d, J=7.0 Hz, O—CH$_2$—CH$_2$); 62.5 (d, J=7.0 Hz, O—CH$_2$—CH$_2$); 168.5 (d, J=5.0 Hz, C=O).

$^{31}$P NMR (160 MHz, CDCl$_3$) δ (ppm): 24.6.

Step E is conducted using sodium hydroxide (8 eq. per 1 eq. of diethyl 1-(N,N-diethylhexylcarbamoyl)nonylphosphonate—reflux for 12 hours) and leads to the title compound (Yield: 99%) for which the $^1$H, $^{13}$C and $^{31}$P NMR characterisations are the following:

$^1$H NMR (400 MHz, CDCl$_3$) δ (ppm): 0.81-0.88 (m, 15H, CH$_3$); 1.20-1.34 (m, 31H, CH$_2$, O—CH$_2$—CH$_3$); 1.55-1.74 (m, 2H, CH—CH$_2$—N); 1.81-1.90 (m, 1H, C$_7$H$_{15}$—CH$_2$—CH—(CO)P); 1.97-2.06 (m, 1H, C$_7$H$_{15}$—CH$_2$—CH—(CO)P); 3.04-3.22 (m, 3H, CH$_2$—N, CO—CH(Oct)-P); 3.28-3.52 (m, 2H, CH$_2$—N); 4.04-4.14 (m, 2H, O—CH$_2$—CH$_3$); 9.35 (ls, 1H, OH).

$^{13}$C NMR (100 MHz, CDCl$_3$) δ (ppm): 10.4; 10.7; 10.8; 14.0; 14.1 (CH$_3$); 16.4 (d, J=6.0 Hz, CH$_3$—CH$_2$—O); 22.6; 23.0; 23.1; 23.4; 23.6; 23.8 (CH$_2$); 28.3 (d, J=3.0 Hz, C$_7$H$_{15}$—CH$_2$—CH—(CO)P); 28.5; 28.6; 28.7; 28.8; 29.2; 29.4; 29.7; 29.8; 30.4; 30.5; 31.8 (CH$_2$); 37.2; 37.3; 38.9; 39.1; 39.3 (CH$_2$—CH$_2$—N); 41.0; 42.3 (d, J=133.5 Hz, CO—CH(Oct)-P); 50.0; 50.5; 50.7; 51.2; 52.0; 52.2; 52.6; 52.8 (CH$_2$—N); 61.9 (d, J=7.0 Hz, O—CH$_2$—CH$_2$); 169.7 (C=O).

$^{31}$P NMR (160 MHz, CDCl$_3$) δ (ppm): 26.8.

I.1.9—2-Ethylhexyl 1-(N,N-diethylhexylcarbamoyl)methylphosphonate

The title compound, denoted DEHCMPEH, which meets particular formula (I-a) wherein m=0, R$^1$=R$^2$=2-ethylhexyl, R$^3$=R$^5$=H, R$^4$=2-ethylhexyl, is synthesised from 1-(N,N-diethylhexylcarbamoyl)methylphosphonic acid obtained under item I.1.1 above, by performing step F.

To do so, 5 molar % DMF is added to a solution of 1-(N,N-diethylhexyl-carbamoyl)methylphosphonic acid (1.84 g-5.7 mmol) in dichloromethane (15 mL) under an inert atmosphere. The mixture is cooled to 0° C. and oxalyl chloride (1.1 mL-12.6 mmol) is added dropwise thereto. The mixture is heated under reflux for one hour. The dichloromethane and excess oxalyl chloride are then distilled. The reaction medium is dissolved in 10 mL of toluene and imidazole (40 mg-0.5 mmol) is added thereto. To this mixture is added dropwise a solution of N,N-diisopropylethylamine (2.2 ml-12.6 mmol) and 2-ethylhexanol (900 μL-5.7 mmol) in toluene (10 mL). The whole is left under agitation for 12 hours after which 5 mL of hydrochloric acid (1 mol/L) are added. The mixture is extracted with dichloromethane (twice). The organic phase is dried over Na$_2$SO$_4$, filtered and concentrated. The product is isolated after purification on a chromatographic column with a dichloromethane/methanol elution gradient: 100:0 to 90:10, v/v.

This leads to the title compound (Yield: 57%) for which the $^1$H, $^{13}$C and $^{31}$P NMR characterisations are the following:

$^1$H NMR (400 MHz, CDCl$_3$) δ (ppm): 0.81-0.87 (m, 18H, CH$_3$); 1.19-1.39 (m, 25H, CH$_2$, O—CH$_2$—CH); 1.50-1.60 (m, 2H, CH—CH$_2$—N; P—O—CH$_2$—CH); 1.64-1.71 (m, 1H, CH—CH$_2$—N); 3.00-3.36 (m, 5H, CO—CH(Oct)-P, CH$_2$—N); 3.90-3.99 (m, 2H, O—CH$_2$—CH); 8.04 (ls, 1H, OH).

$^{13}$C NMR (100 MHz, CDCl$_3$) δ (ppm): 10.5; 10.9; 14.0; 14.1 (CH$_3$); 16.5 (d, J=6.5 Hz, O—CH$_2$—CH); 23.0; 23.1; 23.2; 23.5; 23.7; 28.6; 28.7; 28.9; 29.8; 30.4; 30.5 (CH$_2$); 31.8; 33.1 (d, J=133.0 Hz, CH$_2$—P); 37.0; 38.6 (CH); 40.1 (d, J=6.5 Hz, P—O—CH$_2$—CH); 49.6 (CH$_2$—N); 52.4 (CH$_2$—N); 67.8 (d, J=5.5 Hz, O—CH$_2$—CH); 167.4 (C=O).

$^{31}$P NMR (160 MHz, CDCl$_3$) δ (ppm): 21.6.

I.1.10—Butyl 1-(N,N-diethylhexylcarbamoyl)methylphosphonate

The title compound, denoted DEHCMPB, which meets particular formula (I-a) wherein m=0, $R^1=R^2$=2-ethylhexyl, $R^3=R^5$=H, $R^4$=n-butyl, is synthesised by performing steps A, B and E of the reaction scheme shown in FIG. 1.

Step A is the same as step A described under item I.1.1 above.

Step B is conducted using tributylphosphite (3 eq. per 1 eq. of 2-chloro-N,N-diethylhexylacetamide—reflux for 4 hours) and leads to dibutyl 1-(N,N-diethyl-hexylcarbamoyl)methylphosphonate (Yield: quantitative) for which the $^1$H, $^{13}$C and $^{31}$P NMR characterisations are given below:

$^1$H NMR (400 MHz, CDCl$_3$) δ (ppm): 0.83-0.94 (m, 18H, CH$_3$); 1.23-1.33 (m, 16H, CH$_2$); 1.34-1.43 (m, 4H, O—CH$_2$—CH$_2$—CH$_2$—CH$_3$); 1.53-1.59 (m, 1H, CH—CH$_2$—N); 1.61-1.72 (m, 5H, CH—CH$_2$—N, O—CH$_2$—CH$_2$—CH$_2$—CH$_3$); 3.04 (d, 2H, J=22.0 Hz, CO—CH$_2$—P); 3.23-3.33 (m, 4H, CH$_2$—N); 4.05-4.12 (m, 4H, O—CH$_2$—CH$_2$—CH$_2$—CH$_3$).

$^{13}$C NMR (100 MHz, CDCl$_3$) δ (ppm): 10.4; 10.8 (CH$_3$); 13.5 (O—CH$_2$—CH$_2$—CH$_2$—CH$_3$); 14.1; 14.2 (CH$_3$); 18.2 (O—CH$_2$—CH$_2$—CH$_2$—CH$_3$); 22.9; 23.0, 23.3; 23.8; 28.6; 28.7; 30.2; 30.4 (CH$_2$); 32.4 (d, J=6.0 Hz, O—CH$_2$—CH$_2$—CH$_2$—CH$_3$); 32.8; 34.1 (d, J=133.0 Hz, CH$_2$—P); 36.9; 38.5 (CH); 48.8; 52.2 (CH$_2$—N); 66.1 (d, J=6.5 Hz, O—CH$_2$—CH$_2$—CH$_3$); 165.0 (d, J=6.0 Hz, C=O).

$^{31}$P NMR (160 MHz, CDCl$_3$) δ (ppm): 21.9.

Step E is performed using sodium hydroxide (6 eq. per 1 eq. of dibutyl 1-(N,N-diethylhexylcarbamoyl)methylphosphonate—reflux for 3 hours in a dioxane-water mixture) and leads to the title compound (Yield: 99%) for which the $^1$H, $^{13}$C and $^{31}$P NMR characterisations are as follows:

$^1$H NMR (400 MHz, CDCl$_3$) δ (ppm): 0.83-0.94 (m, 15H, CH$_3$); 1.23-1.33 (m, 16H, CH$_2$); 1.35-1.43 (m, 2H, O—CH$_2$—CH$_2$—CH$_2$—CH$_3$); 1.55-1.73 (m, 4H, CH—CH$_2$—N, O—CH$_2$—CH$_2$—CH$_2$—CH$_3$); 3.03 (d, 2H, J=21.5 Hz, CO—CH$_2$—P); 3.27-3.37 (m, 4H, CH$_2$—N); 4.05-4.10 (q, 4H, J=7.0 Hz, O—CH$_2$—CH$_2$—CH$_2$—CH$_3$); 11.94 (ls, 1H, OH).

$^{13}$C NMR (100 MHz, CDCl$_3$) δ (ppm): 10.4; 10.8 (CH$_3$); 13.5 (O—CH$_2$—CH$_2$—CH$_2$—CH$_3$); 14.1; 14.2 (CH$_3$); 18.2 (O—CH$_2$—CH$_2$—CH$_2$—CH$_3$); 22.9; 23.0, 23.3; 23.8; 28.6; 28.7; 30.2; 30.4 (CH$_2$); 32.4 (d, J=6.0 Hz, O—CH$_2$—CH$_2$—CH$_2$—CH$_3$); 32.8; 34.1 (d, J=133.0 Hz, CH$_2$—P); 36.9; 38.5 (CH); 48.8; 52.2 (CH$_2$—N); 66.1 (d, J=6.5 Hz, O—CH$_2$—CH$_2$—CH$_3$); 165.0 (d, J=6.0 Hz, C=O).

$^{31}$P NMR (160 MHz, CDCl$_3$) δ (ppm): 21.9.

I.1.11—Butyl 1-(N,N-diethylhexylcarbamoyl)nonylphosphonate

The title compound, denoted DEHCNPB, which meets particular formula (I-a) wherein m=0, $R^1=R^2$=2-ethylhexyl, $R^3$=H, $R^4$=n-butyl and $R^5$=n-octyl, is synthesised by performing steps A, B, C and E of the reaction scheme shown in FIG. 1.

Step A is the same as step A described under item I.1.1 above.

Step B is the same as step B described under item I.1.10 above.

Step C is conducted using octyl iodide and leads to dibutyl 1-(N,N-diethylhexylcarbamoyl)nonylphosphonate (Yield: 99%) for which the $^1$H, $^{13}$C and $^{31}$P characterisations are the following:

$^1$H NMR (400 MHz, CDCl$_3$) δ (ppm): 0.81-0.93 (m, 21H, CH$_3$); 1.17-1.42 (m, 32H, CH$_2$, O—CH$_2$—CH$_2$—CH$_2$—CH$_3$); 1.59-1.66 (m, 5H, CH—CH$_2$—N, O—CH$_2$—CH$_2$—CH$_2$—CH$_3$); 1.69-1.84 (m, 2H, CH—CH$_2$—N, C$_7$H$_{15}$—CH$_2$—CH—(CO)P); 2.02-2.13 (m, 1H, C$_7$H$_{15}$—CH$_2$—CH—(CO)P); 2.80-2.92 (m, 1H, CH$_2$—N); 2.95-3.03 (m, 1H, CH$_2$—N); 3.14-3.22 (m, 1H, CO—CH(Oct)-P); 3.43-3.55 (m, 1H, CH$_2$—N); 3.62-3.78 (m, 1H, CH$_2$—N); 3.96-4.11 (m, 4H, O—CH$_2$—CH$_2$—CH$_2$—CH$_3$).

$^{13}$C NMR (100 MHz, CDCl$_3$) δ (ppm): 10.4; 10.7; 10.9; 11.0 (CH$_3$); 13.8 (O—CH$_2$—CH$_2$—CH$_2$—CH$_3$); 14.2; 14.3 (CH$_3$); 18.9 (O—CH$_2$—CH$_2$—CH$_2$—CH$_3$); 22.8; 23.2; 23.3; 23.7; 23.9; 24.0; (CH$_2$); 28.2 (C$_7$H$_{15}$—CH$_2$—CH—(CO)P); 28.8; 28.9; 29.0; 29.1; 29.4; 29.5; 29.8; 29.9; 30.4; 30.5; 30.7; 30.8; 32.0 (CH$_2$); 32.7; 32.8 (d, J=6.5 Hz, O—CH$_2$—CH$_2$—CH$_2$—CH$_3$); 37.2; 37.3; 37.4; 39.2; 39.3; 39.5; 39.6 (CH—CH$_2$—N); 41.9; 43.2 (d, J=131.0 Hz, CO—CH(Oct)-P); 50.0; 50.2; 50.9; 51.1; 51.9; 52.0; 52.6; 52.7 (CH$_2$—N); 66.1 (d, J=6.5 Hz, O—CH$_2$—CH$_2$); 66.3 (d, J=6.5 Hz, O—CH$_2$—CH$_2$); 168.5 (d, J=5.0 Hz, C=O).

$^{31}$P NMR (160 MHz, CDCl$_3$) δ (ppm): 24.6.

Step E is performed using sodium hydroxide (8 eq. per 1 eq. of dibutyl 1-(N,N-diethylhexylcarbamoyl)nonylphosphonate—reflux for 15 hours in a dioxane-water mixture) and leads to the title compound (Yield: 99%) for which the $^1$H, $^{13}$C and $^{31}$P NMR characterisations are the following:

$^1$H NMR (400 MHz, CDCl$_3$) δ (ppm): 0.83-0.94 (m, 18H, CH$_3$); 1.20-1.41 (m, 30H, CH$_2$, O—CH$_2$—CH$_2$—CH$_2$—CH$_3$); 1.59-1.73 (m, 4H, O—CH$_2$—CH$_2$—CH$_2$—CH$_3$, C$_7$H$_{15}$—CH$_2$—CH—(CO)P); 1.85-2.06 (m, 2H, CH—CH$_2$—N); 3.07-3.21 (m, 3H, CH$_2$—N, CO—CH(Oct)-P); 3.24-3.50 (m, 2H, CH—N); 3.98-4.10 (m, 2H, O—CH$_2$—CH$_2$—CH$_2$—CH$_3$); 9.34 (s, 1H, OH).

$^{13}$C NMR (100 MHz, CDCl$_3$) δ (ppm): 10.5; 10.8; 10.9; (CH$_3$); 13.7 (O—CH$_2$—CH$_2$—CH$_2$—CH$_3$); 14.1; 14.2 (CH$_3$); 18.8 (O—CH$_2$—CH$_2$—CH$_2$—CH$_3$); 22.8; 23.2; 23.3; 23.7; 23.8; 23.9; (CH$_2$); 28.2 (C$_7$H$_{15}$—CH$_2$—CH—(CO)P); 28.7; 28.9; 29.4; 29.5; 29.8; 29.9; 30.4; 30.5; 30.7; 32.0 (CH$_2$); 32.6 (d, J=6.5 Hz, O—CH$_2$—CH$_2$—CH$_2$—CH$_3$); 37.2; 37.3; 39.0; 39.2; 39.4 (CH—CH$_2$—N); 41.9; 43.2 (d, J=134.0 Hz, CO—CH(Oct)-P); 49.9; 50.5; 50.7; 51.2; 52.0; 52.1; 52.7; 52.8 (CH$_2$—N); 65.6 (d, J=6.5 Hz, O—CH$_2$—CH$_2$); 169.3 (d, J=5.0 Hz, C=O).

$^{31}$P NMR (160 MHz, CDCl$_3$) δ (ppm): 26.8.

I.1.12—Butyl 1-(N,N-dioctylcarbamoyl)nonylphosphonate

The title compound, denoted DOCNPB, which meets particular formula (I-a) wherein m=0, $R^1=R^2$=n-octyl, $R^3$=H, $R^4$=n-butyl and $R^5$=n-octyl, is synthesised by performing steps A, B, C and E of the reaction scheme shown in FIG. 1.

Step A is conducted using dioctylamine and chloroacetyl chloride and leads to 2-chloro-N,N-dioctylacetamide (Yield: 96%) for which the $^1H$ and $^{13}C$ NMR characterisations are the following:

$^1H$ NMR (400 MHz, CDCl$_3$) δ (ppm): 0.81-0.86 (m, 6H, CH$_3$); 1.21-1.27 (m, 20H, CH$_2$); 1.45-1.58 (m, 4H, CH$_2$—CH$_2$N); 3.20-3.29 (m, 4H, CH—N); 4.01 (s, 2H, CH$_2$Cl).

$^{13}C$ NMR (100 MHz, CDCl$_3$) δ (ppm): 14.1 (CH$_3$); 22.6; 26.8; 26.9 (CH$_2$); 27.4; 29.1 (CH$_2$—CH$_2$—N); 29.2; 29.3; 29.4; 31.7; 31.8 (CH$_2$); 41.3 (CH$_2$—Cl); 46.3; 48.3 (CH$_2$—N); 166.0 (C=O).

Step B is conducted using tributylphosphite (3 eq. per 1 eq. of 2-chloro-N,N-dioctylacetamide—reflux for 4 hours) and leads to dibutyl 1-(N,N-dioctyl-carbamoyl)methylphosphonate (Yield: quantitative) for which the $^1H$, $^{13}C$ and $^{31}P$ NMR characterisations are given below:

$^1H$ NMR (400 MHz, CDCl$_3$) δ (ppm): 0.83-0.94 (m, 12H, CH$_3$); 1.23-1.33 (m, 20H, CH$_2$); 1.34-1.44 (m, 4H, O—CH$_2$—CH$_2$—CH$_2$—CH$_3$); 1.47-1.58 (m, 4H, CH$_2$—CH$_2$—N); 1.61-1.69 (m, 4H, O—CH$_2$—CH$_2$—CH$_2$—CH$_3$); 3.00 (d, 2H, J=22.0 Hz, CO—CH$_2$—P); 3.27-3.33 (m, 4H, CH$_2$—N); 4.05-4.12 (q, 4H, J=7.0 Hz; O—CH$_2$—CH$_2$—CH$_3$).

$^{13}C$ NMR (100 MHz, CDCl$_3$) δ (ppm): 13.4 (O—CH$_2$—CH$_2$—CH$_2$—CH$_3$); 13.9 (CH$_3$); 18.5 (O—CH$_2$—CH$_2$—CH$_2$—CH$_3$); 22.4; 26.6, 26.7 (CH$_2$); 27.5; 28.8 (CH$_2$—CH$_2$—N); 29.0; 29.1; 29.1; 29.2; 31.5; 31.6 (CH$_2$); 32.4 (d, J=6.0 Hz, O—CH$_2$—CH$_2$—CH$_2$—CH$_3$); 32.5; 33.8 (d, J=133.0 Hz, CH$_2$—P); 46.0; 48.6 (CH$_2$—N); 66.0 (d, J=6.5 Hz, O—CH$_2$—CH$_2$—CH$_2$—CH$_3$); 164.0 (d, J=6.0 Hz, C=O).

$^{31}P$ NMR (160 MHz, CDCl$_3$) δ (ppm): 21.6.

Step C is conducted using octyl iodide and leads to dibutyl 1-(N,N-dioctylcarbamoyl)nonylphosphonate (Yield: 99%) for which the $^1H$, $^{13}C$ and $^{31}P$ NMR characterisations are the following:

$^1H$ NMR (400 MHz, CDCl$_3$) δ (ppm): 0.80-0.88 (m, 15H, CH$_3$); 1.13-1.40 (m, 36H, CH$_2$); 1.35-1.43 (m, 4H, O—CH$_2$—CH$_2$—CH$_2$—CH$_3$); 1.49-1.56 (m, 3H, CH$_2$—CH$_2$—N); 1.59-1.69 (m, 5H, CH$_2$—CH$_2$—N; O—CH$_2$—CH$_2$—CH$_2$—CH$_3$); 1.75-1.84 (m, 1H, C$_7$H$_{15}$—CH$_2$—CH—(CO)P); 2.02-2.13 (m, 1H, C$_7$H$_{15}$—CH$_2$—CH—(CO)P); 3.04-3.21 (m, 3H, CH$_2$—CH$_2$—N; C$_7$H$_{15}$—CH$_2$—CH—(CO)P); 3.38-3.57 (m, 2H, CH$_2$—CH$_2$—N); 3.98-4.13 (m, 4H, O—CH$_2$—CH$_2$—CH$_2$—CH$_3$).

$^{13}C$ NMR (100 MHz, CDCl$_3$) δ (ppm): 13.5 (CH$_3$—CH$_2$—CH$_2$—CH$_2$—O); 14.1 (CH$_3$); 18.7 (CH$_3$—CH$_2$—CH$_2$—CH$_2$—O); 22.6; 26.8; 26.9; 27.0; 27.5; 27.6; 27.9; 28.4; 29.6; 29.1; 29.2; 29.3; 29.4; 31.7; 31.8 (CH$_2$); 32.6 (d, J=6.0 Hz, CH$_3$—CH$_2$—CH$_2$—CH$_2$—O); 41.5; 42.8 (d, J=132.0 Hz, C$_7$H$_{15}$CHC(O)P(O)); 46.9; 48.4 (CH$_2$—N); 66.0 (d, J=6.5 Hz, O—CH$_2$—CH$_2$—CH$_2$—CH$_3$)); 66.2 (d, J=6.5 Hz, O—CH$_2$—CH$_2$—CH$_2$—CH$_3$)); 167.6 (d, J=4.5 Hz, C=O).

$^{31}$ NMR (160 MHz, CDCl$_3$) δ (ppm): 24.6.

Step E is conducted using sodium hydroxide (8 eq. per 1 eq. of dibutyl 1-(N,N-dioctylcarbamoyl)nonylphosphonate—reflux for 15 hours) and leads to the title compound (Yield: 99%) for which the $^1H$, $^{13}C$ and $^{31}P$ NMR characterisations are the following:

$^1H$ NMR (400 MHz, CDCl$_3$) δ (ppm): 0.83-0.91 (m, 12H, CH$_3$); 1.22-1.43 (m, 34H, CH$_2$, O—CH$_2$—CH$_2$—CH$_2$—CH$_3$); 1.49-1.56 (m, 3H, CH$_2$—CH$_2$—N); 1.59-1.69 (m, 3H, (CH$_2$—CH$_2$—N; O—CH$_2$—CH$_2$—CH$_2$—CH$_3$); 1.80-1.88 (m, 1H, C$_7$H$_{15}$—CH$_2$—CH—(CO)P); 1.99-2.10 (m, 1H, C$_7$H$_{15}$—CH$_2$—CH—(CO)P); 3.07-3.23 (m, 3H, CH$_2$—CH$_2$—N; C$_7$H$_{15}$—CH$_2$—CH—(CO)P); 3.36-3.48 (m, 2H, CH$_2$—CH$_2$—N); 3.97-4.09 (m, 2H, O—CH$_2$—CH$_2$—CH$_3$); 11.05 (ls, 1H, OH).

$^{13}C$ NMR (100 MHz, CDCl$_3$) δ (ppm): 13.8 (CH$_3$—CH$_2$—CH$_2$—CH$_2$—O); 14.1 (CH$_3$); 18.9 (CH$_3$—CH$_2$—CH$_2$—CH$_2$—O); 22.8; 27.1; 27.2; 27.0; 27.7; 28.0; 28.1; 28.7; 28.8; 29.4; 29.5; 29.6; 29.8; 31.9; 32.0 (CH$_2$); 32.7 (d, J=6.0 Hz, CH$_3$—CH$_2$—CH$_2$—CH$_2$—O); 41.2; 42.4 (d, J=132.0 Hz, C$_7$H$_{15}$CHC(O)P(O)); 47.3; 48.8 (CH$_2$—N); 65.8 (d, J=6.5 Hz, O—CH$_2$—CH$_2$—CH$_2$—CH$_3$); 66.2 (d, J=6.5 Hz, O—CH$_2$—CH$_2$—CH$_2$—CH$_3$); 168.7 (d, J=4.5 Hz, C=O).

$^{31}P$ NMR (160 MHz, CDCl$_3$) δ (ppm): 26.5.

I.1.13—2-(N,N-diethylhexylcarbamoyl)ethylphosphonic acid

The title compound, denoted ADEHCEP, which meets particular formula (I-a) wherein m=1, $R^1$=$R^2$=2-ethylhexyl, $R^3$=$R^4$=$R^5$=H is synthesised by performing steps A, B and D of the reaction scheme shown in FIG. 1.

Step A is conducted using 2,2'-diethylhexylamine and 3-bromo-propanoyl chloride and leads to 3-bromo-N,N-bis (2-ethylhexyl)propanamide (Yield: 97%) for which the $^1H$ and $^{13}C$ NMR characterisations are given below:

$^1H$ NMR (400 MHz, CDCl$_3$) δ (ppm): 0.78-0.85 (m, 12H, CH$_3$); 1.14-1.28 (m, 16H, CH$_2$); 1.49-1.56 (m, 1H, CH—CH$_2$—N); 1.58-1.64 (m, 1H, CH—CH$_2$—N); 2.85 (t, 2H, J=7.0 Hz, CO—CH$_2$); 3.20 (d, 2H, J=7.5 Hz, CH$_2$—N); 3.26-3.32 (m, 2H, CH$_2$—N); 3.60 (t, 2H, J=7.0 Hz, CH$_2$—Br).

$^{13}C$ NMR (100 MHz, CDCl$_3$) δ (ppm): 10.8 (CH$_3$—CH$_2$—CH); 14.1 (CH$_3$); 23.0; 23.1; 23.9 (CH$_2$); 28.0 (CH$_2$—Br); 28.8; 30.5; 30.6 (CH$_2$); 36.6 (CO—CH$_2$); 37.0; 38.5 (CH); 49.2 (CH$_2$—N); 51.5 (CH$_2$—N); 170.4 (C=O).

Step B is conducted using triethylphosphite (4 eq. per 1 eq. of 3-bromo-N,N-bis(2-ethylhexyl)propanamide—reflux for 6 hours) and leads to diethyl 2-(N,N-diethylhexylcarbamoyl)ethylphosphonate (Yield: quantitative) for which the $^1H$, $^{13}C$ and $^{31}P$ NMR characterisations are the following:

$^1H$ NMR (400 MHz, CDCl$_3$) δ (ppm): 0.81-0.89 (m, 12H, CH$_3$); 1.18-1.35 (m, 22H, CH$_2$, O—CH$_2$—CH$_3$); 1.53-1.67 (m, 2H, CH—CH$_2$—N); 2.04-2.13 (m, 2H, CH$_2$—P); 2.55-2.61 (m, 2H, CO—CH$_2$); 3.12 (d, 2H, J=7.5 Hz, CH$_2$—N); 3.18-3.32 (m, 2H, CH$_2$—N); 4.02-4.12 (m, 4H, O—CH$_2$—CH$_3$).

$^{13}C$ NMR (100 MHz; CDCl$_3$) δ (ppm): 10.6; 10.8; 14.0; 14.1 (CH$_3$); 16.4; 16.5 (O—CH$_2$—CH$_3$); 21.2 (d; J=134.0 Hz; CH$_2$—P); 23.0; 23.1; 23.8; 23.9 (CH$_2$); 26.6 (CO—CH$_2$); 28.7; 28.8; 30.5; 30.6 (CH$_2$); 37.0; 38.4 (CH); 49.0 (CH$_2$—N); 51.2 (CH$_2$—N); 61.6 (d, J=6.5 Hz, O—CH$_2$—CH$_3$); 171.2 (d, J=18.0 Hz, C=O).

$^{31}P$ NMR (160 MHz, CDCl$_3$) δ (ppm): 32.1.

Step D leads to the title compound (Yield: quantitative) for which the $^1H$, $^{13}C$, $^{31}P$ NMR characterisations are the following:

$^1H$ NMR (400 MHz, CDCl$_3$) δ (ppm): 0.82-0.90 (m, 12H, CH$_3$); 1.22-1.34 (m, 16H, CH$_2$); 1.59-1.68 (m, 2H, CH—CH$_2$—N); 2.04 (dt, 2H, J=18.5 HZ, 6.5 Hz, CH$_2$—P); 2.76 (dt, 2H, J=20.5 HZ, 6.5 Hz, CO—CH$_2$); 3.15 (d, 2H, J=7.5 Hz, CH$_2$—N); 3.20-3.34 (m, 2H, CH$_2$—N); 8.34 (ls, 2H, OH).

$^{13}C$ NMR (100 MHz; CDCl$_3$) δ (ppm): 10.6; 10.8; 14.0; 14.1 (CH$_3$); 22.0; 23.4 (d, J=135.0 Hz, CH$_2$—P); 26.8 (d, J=4.5 Hz, CO—CH$_2$); 28.6; 28.7; 30.4; 30.5 (CH$_2$); 37.0; 38.4 (CH); 49.8 (CH$_2$—N); 52.0 (CH$_2$—N); 174.3 (d, J=6.0 Hz, C=O).

$^{31}$P NMR (160 MHz, CDCl$_3$) δ (ppm): 31.1.

I.1.14—3-(Diéthylhexylcarbamoyl)propylphosphonic acid

The title compound, denoted ADEHCPP, which meets particular formula (I-a) wherein m=2, R$^1$=R$^2$=2-ethylhexyl, R$^3$=R$^4$=R$^5$=H is synthesised by performing steps A, B and D of the reaction scheme shown in FIG. 1.

Step A is conducted starting from 2,2'-diethylhexylamine and 4-chlorobutanoyl chloride and leads to 4-chloro-N,N-bis(2-ethylhexyl)butanamide (Yield: quantitative) for which the $^1$H and $^{13}$C NMR characterisations give:

$^1$H NMR (400 MHz, CDCl$_3$) δ (ppm): 0.86-0.93 (m, 12H, CH$_3$); 1.25-1.35 (m, 16H, CH$_2$); 1.58-1.73 (m, 2H, CH—CH$_2$—N); 2.11-2.17 (m, 2H, CH$_2$—CH$_2$—Cl); 2.53 (t, 2H, J=7.0 Hz, CO—CH$_2$); 3.18 (d, 2H, J=7.5 Hz, CH$_2$—N); 3.26-3.32 (m, 2H, CH$_2$—N); 3.64 (t, 2H, J=6.0 Hz, CH$_2$—Cl).

$^{13}$C NMR (100 MHz, CDCl$_3$) δ (ppm): 10.7; 10.9 (CH$_3$—CH$_2$—CH); 14.1 (CH$_3$); 23.1; 23.9 (CH$_2$); 28.2 (CH$_2$—CH$_2$—Cl); 28.7 (CH$_2$); 30.0 (CO—CH$_2$); 30.6 (CH$_2$); 37.0; 38.5 (CH); 45.0 (CH$_2$—Cl); 49.0 (CH$_2$—N); 51.4 (CH$_2$—N); 172.1 (C=O).

Step B is conducted using triethylphosphite (4 eq. per 1 eq. of 4-chloro-N,N-bis(2-ethylhexyl)butanamide—reflux for 48 hours) and leads to diethyl 3-(N,N-diethylhexylcarbamoyl)propylphosphonate (Yield: 68%) for which the $^1$H, $^{13}$C and $^{31}$P NMR characterisations are the following:

$^1$H NMR (400 MHz, CDCl$_3$) δ (ppm): 0.81-0.87 (m, 12H, CH$_3$); 1.13-1.30 (m, 22H, CH$_2$, O—CH$_2$—CH$_3$); 1.51-1.57 (m, 1H, CH—CH$_2$—N); 1.59-1.65 (m, 1H, CH—CH$_2$—N); 1.74-1.85 (dd, 2H, J=18.0 Hz, 8.5 Hz, CO—CH$_2$—CH$_2$—P); 1.87-1.97 (m, 2H, CO—CH$_2$—CH$_2$—CH$_2$—P); 2.40 (t, 2H, J=7.0 Hz, CO—CH$_2$—CH$_2$—CH$_2$—P); 3.09 (d, 2H, J=7.5 Hz, CH$_2$—N); 3.16-3.30 (m, 2H, CH$_2$—N); 4.00-4.10 (m, 4H, O—CH$_2$—CH$_3$).

$^{13}$C NMR (100 MHz, CDCl$_3$) δ (ppm): 10.7; 10.9; 14.0; 14.1 (CH$_3$); 16.4; 16.5 (O—CH$_2$—CH$_3$); 18.6 (d, J$_{C—P}$=4.5 Hz, CO—CH$_2$—CH$_2$—CH$_2$—P), 23.0; 23.1; 23.8; 23.9 (CH$_2$); 24.5; 25.9 (d; J$_{C—P}$=140.0 Hz; CO—CH$_2$—CH$_2$—CH$_2$—P); 28.7; 28.8; 30.5; 30.6 (CH$_2$); 33.6 (d, J$_{C—P}$=14.5 Hz; CO—CH$_2$—CH$_2$—CH$_2$—P); 37.0; 38.4 (CH—CH$_2$—N); 48.6; 51.3 (CH$_2$—N); 61.5 (d, J=6.5 Hz, O—CH$_2$—CH$_3$); 172.3 (C=O).

$^{31}$P NMR (160 MHz, CDCl$_3$) δ (ppm): 31.8.

Step D leads to the title compound (Yield: quantitative) for which the $^1$H, $^{13}$C, $^{31}$P characterisations are given below:

$^1$H NMR (400 MHz, CDCl$_3$) δ (ppm): 0.81-0.88 (m, 12H, CH$_3$); 1.15-1.31 (m, 16H, CH$_2$); 1.52-1.58 (m, 1H, CH—CH$_2$—N); 1.60-1.66 (m, 1H, CH—CH$_2$—N); 1.77 (dt, 2H, J=18.5 Hz, 7.5 Hz, CO—CH$_2$—CH$_2$—CH$_2$—P); 1.90-2.01 (m, 2H, CO—CH$_2$—CH$_2$—CH$_2$—P); 2.48 (t, 2H, J=7.5 Hz, CO—CH$_2$—CH$_2$—CH$_2$—P); 3.11 (d, 2H, J=7.5 Hz, CH$_2$—N); 3.15-3.34 (m, 2H, CH$_2$—N); 9.33 (ls, 2H, OH).

$^{13}$C NMR (100 MHz, CDCl$_3$) δ (ppm): 10.8; 11.1; 14.2; 14.3 (CH$_3$); 19.2 (d, J=4.0 Hz, CO—CH$_2$—CH$_2$—CH$_2$—P); 23.2; 23.3; 24.0 (CH$_2$); 25.6; 27.0 (d, J=140.0 Hz, CO—CH$_2$—CH$_2$—CH$_2$—P); 28.9; 29.0; 30.7; 30.8 (CH$_2$); 30.5; 30.6 (d, J=12.0 Hz, CO—CH$_2$—CH$_2$—CH$_2$—P); 37.1; 38.6 (CH); 49.0 (CH$_2$—N); 51.4 (CH$_2$—N); 174.0 (C=O).

$^{31}$P NMR (160 MHz, CDCl$_3$) δ (ppm): 31.5.

Figure 2:
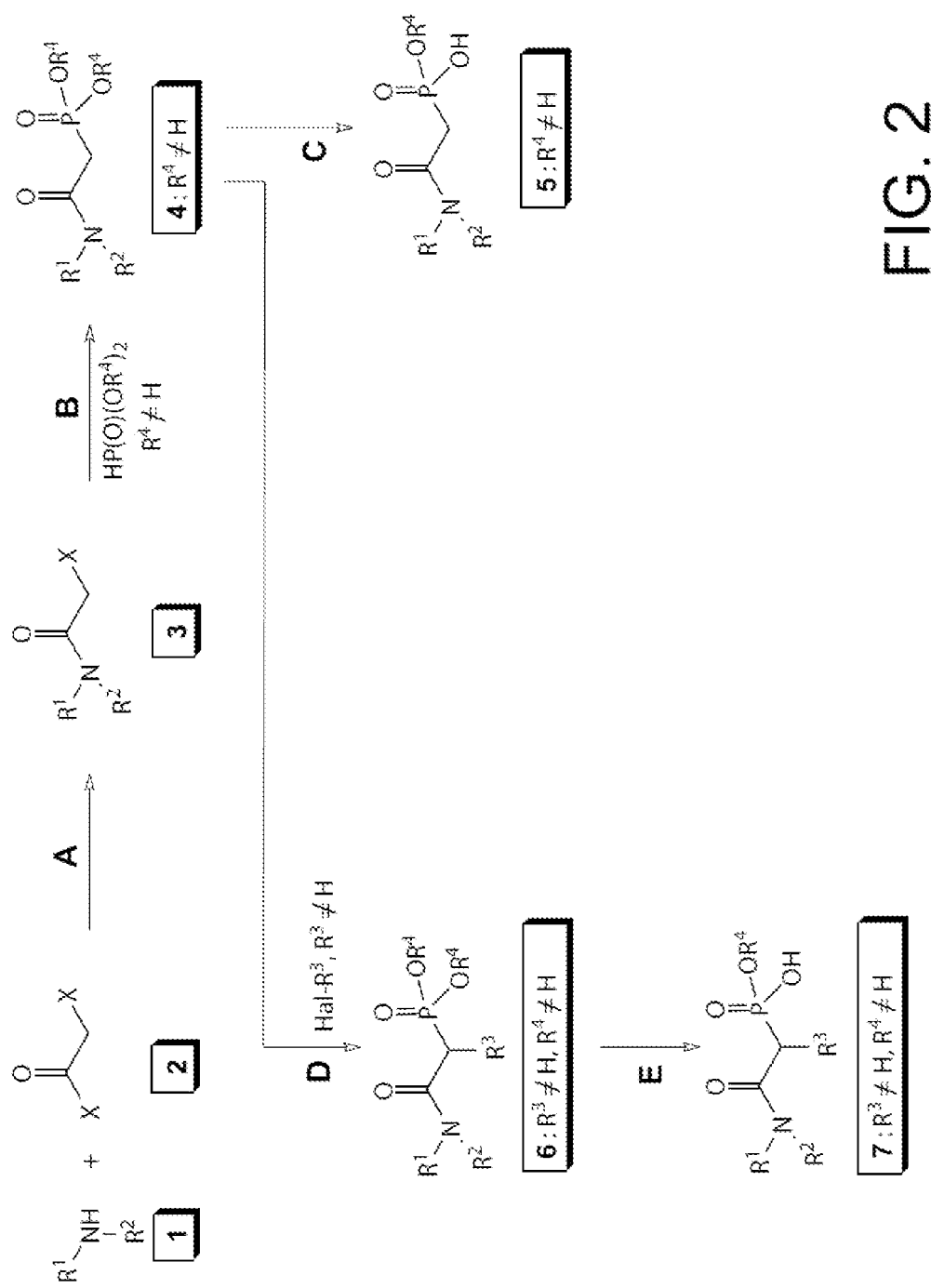
FIG. 2 illustrates the steps of methods for synthesising compounds of the invention which meet particular formula (I-a) wherein m=0, $R^4$ differs from a hydrogen atom whilst $R^5$ is a hydrogen atom.

I.2—Synthesis of Compounds of Particular Formula (I-a) Wherein m=0, R$^4$≠H and R$^5$=H The compounds meeting particular formula (I-a) above wherein m=0, R$^1$, R$^2$, R$^3$ have the same meaning as previously, R$^4$ differs from a hydrogen atom whilst R$^5$ is a hydrogen atom can also be synthesised following the reaction scheme illustrated in FIG. 2.

As can be seen in this Figure, this synthesis at a first step denoted A entails causing an amine denoted 1 to react with a halide of a halogenoacetyl (for example a chloroacetyl chloride) denoted 2, to obtain compound 3.

This step is performed for example in the presence of triethylamine in an organic solvent of dichloromethane type.

At a second step, denoted B in FIG. 2, compound 3 is caused to react with a phosphite HP(O)(OR$^4$)$_2$ wherein R$^4$ differs from a hydrogen atom, to obtain compound 4 wherein R$^4$ differs from a hydrogen atom.

This step is conducted for example in the presence of n-butyllithium and 2,2'-bipyridine (the latter acting as coloured indictor) or sodium hydride in an organic solvent of tetrahydrofuran type.

Resulting compound 4 is then subjected:
either to a monosaponification step, denoted C in FIG. 2, through the action of a strong base e.g. potash in a solvent composed of water and dimethylformamide, to obtain compound 5 wherein R$^3$ is a hydrogen atom whilst R$^4$ differs from a hydrogen atom;
or to a C-alkylation step, denoted D in FIG. 2, through the reaction of compound 4 with a halide Hal-R$^3$ wherein R$^3$ differs from a hydrogen atom, to alkylate this compound at α of the amide group and obtain compound 6 wherein R$^3$ and R$^4$ both differ from a hydrogen atom.

Step D is conducted for example in the presence of n-butyllithium and 2,2'-pyridine, or sodium hydride and 2,2'-pyridine, in an organic solvent of tetrahydrofuran type.

Compound 6 obtained after this step is then subjected to a monosaponification step, denoted E in FIG. 2, which can be performed in the same manner as in step C to obtain compound 7 wherein R$^3$ and R$^4$ both differ from a hydrogen atom.

The following compounds are thus synthesised:

I.2.1—Butyl 1-(N,N-diethylhexylcarbamoyl)nonylphosphonate

Butyl 1-(N,N-diethylhexylcarbamoyl)nonylphosphonate, denoted DEHCNPB, which meets particular formula (I-a) above wherein m=0, R$^1$=R$^2$=2-ethylhexyl, R$^3$=n-octyl, R$^4$=n-butyl and R$^5$=H, is synthesised by performing steps A, B, D and E shown in FIG. 2.

Step A: Synthesis of 2-chloro-N,N-diethylhexylacetamide

To a three-necked flask under agitation and under nitrogen are added 7.46 mL (2 eq.) of bis(2-ethylhexyl)-amine, 50 mL of dichloromethane and 3.5 mL (2 eq.) of triethylamine that are cooled to −30° C. with a dry ice/acetone bath. 2 mL (1 eq.) of chloroacetyl chloride are added dropwise and the reaction medium is left for 3 hours at ambient temperature.

After this time, it is poured onto 50 mL of distilled water, decanted and the aqueous phase extracted with 50 mL of dichloromethane. The dichloromethane phases are washed with 50 mL of distilled water, dried over magnesium sulphate, filtered and evaporated to dryness in a rotary evaporator. The 7.26 g of yellow oil thus obtained are subjected to silica gel column chromatography (80 g-63-200 μm particle size) using a dichloromethane/methanol mixture 98:2 v/v as eluent.

In this manner 7.20 g of 2-chloro-N,N-diethylhexylacetamide in the form of a pale yellow oil (Yield: 92%) are obtained for which the characterisations by $^1$H and $^{13}$C NMR and mass spectrometry are given below.

$^1$H NMR (400 MHz, CDCl$_3$) δ (ppm): 4.08 (2H, s, CH$_2$Cl); 3.23-3.28 (2H, m, NCH$_2$); 3.20 (2H, d, J=7.5 Hz, NCH$_2$); 1.76-1.65 (1H, m, NCH$_2$CH); 1.64-1.52 (1H, m, NCH$_2$CH); 1.40-1.15 (16H, m, CH$_3$(CH$_2$)$_3$CH(CH$_2$CH$_3$)CH$_2$N); 0.95-0.78 (12H, m, CH$_3$).

$^{13}$C NMR (100.13 MHz, CDCl$_3$) δ (ppm): 166.64 (C=O); 51.27 (NCH$_2$); 48.3 (NCH$_2$); 41.17 (CH$_2$Cl); 38.10 (CH); 36.40 (CH); 30.16 (NCH$_2$CH(Et)CH$_2$(CH$_2$)$_2$CH$_3$); 30.00 (NCH$_2$CH(Et)-CH$_2$(CH$_2$)$_2$CH$_3$); 28.40 (NCH$_2$CH(Et)CH$_2$CH$_2$CH$_2$CH$_3$); 28.24 (NCH$_2$CH(Et)CH$_2$CH$_2$CH$_2$CH$_3$); 23.49 (—CHCH$_2$CH$_3$); 23.35 (—CHCH$_2$CH$_3$); 22.65 (NCH$_2$CH(Et)-CH$_2$CH$_2$CH$_2$CH$_3$); 22.62 (NCH$_2$CH(Et)CH$_2$CH$_2$CH$_2$CH$_3$); 13.67 (—CH$_2$CH$_2$CH$_3$); 13.63 (—CH$_2$CH$_2$CH$_3$); 10.49 (—CHCH$_2$CH$_3$); 10.20 (—CHCH$_2$CH$_3$).

ESI$^+$: [M+H]=318, [M+Na]=340, [2M+Na]=657

Step B: Synthesis of dibutyl 1-(N,N-diethylhexylcarbamoyl)methylphosphonate

To a three-necked flask under agitation and under nitrogen are added 1 mL (1 eq.) of dibutylphosphite, a few crystals of 2,2'-bipyridine and 50 mL of tetrahydrofuran; these are cooled to −50° C. using a dry ice/acetone bath. 4.6 mL (1.5 eq.) of a 1.6 mol/L n-butyllithium solution in hexane are added dropwise. A clear red reaction mixture is obtained. To this is added dropwise 1.95 g (1.25 eq.) of 2-chloro-N,N-diethylhexylacetamide. A yellow reaction mixture is obtained which is left overnight at ambient temperature. After this time it is poured onto 100 mL of distilled water and acidified through the addition of 1 N HCl in a sufficient amount to obtain an acid pH. The aqueous phase is extracted with twice 50 mL ethyl ether. The ether phases are washed with twice 50 mL distilled water and 50 mL NaCl-saturated water, dried over magnesium sulphate, filtered and evaporated to dryness in a rotary evaporator. The 2.69 g of yellow oil obtained are subjected to silica gel column chromatography (125 g-63-200 μm particle size) using a cyclohexane/ethyl acetate mixture 8:2 v/v for elution.

In this manner 1.03 g of dibutyl 1-(N,N-diethylhexylcarbamoyl)methyl-phosphonate are obtained in the form of a colourless oil (Yield: 44%) for which the characterisations by $^1$H, $^{13}$C and $^{31}$P NMR and by mass spectrometry are given below.

$^1$H NMR (400 MHz, CDCl$_3$) δ (ppm): 4.18-4.04 (4H, m, OCH$_2$); 3.37-3.20 (4H, m, NCH$_2$); 3.07 (2H, d, J=22 Hz, COCH$_2$P); 1.78-1.51 (6H, m, OCH$_2$CH$_2$, CH); 1.47-1.14 (20H, m, OCH$_2$CH$_2$CH$_2$, CH$_3$(CH$_2$)$_3$CH(CH$_2$CH$_3$)CH$_2$N); 0.99-0.82 (18H, m, CH$_3$).

$^{13}$C NMR (100.13 MHz, CDCl$_3$) δ (ppm): 165.15 (C=O); 66.15 (d, $^2J_{PC}$=6.6 Hz); 52.26 (NCH$_2$); 48.86 (NCH$_2$), 38.58 (CH); 36.98 (CH); 33.61 (d, $^1J_{PC}$=133 Hz; CH$_2$P); 30.52 and 30.27 (NCH$_2$CH(Et)CH$_2$(CH$_2$)$_2$CH$_3$); 30.17 (OCH$_2$CH$_2$CH$_2$CH$_3$); 28.81 and 28.67 (NCH$_2$CH(Et)CH$_2$CH$_2$CH$_2$CH$_3$); 26.86 (OCH$_2$CH$_2$CH$_2$CH$_3$); 23.83 and 23.39 (—CHCH$_2$CH$_3$); 23.11 and 23.03 (NCH$_2$CH(Et)CH$_2$CH$_2$CH$_2$CH$_3$); 18.72 (OCH$_2$CH$_2$CH$_2$CH$_3$); 14.12 and 14.03 (OCH$_2$CH$_2$CH$_2$CH$_3$); 13.61 (CH$_2$CH$_2$CH$_3$); 10.91 and 10.51 (—CHCH$_2$CH$_3$).

$^{31}$P NMR (162 MHz, CDCl$_3$, $^1$H decoupling) δ (ppm): 22.03 (s, P=O)

ESI$^+$: [M+H]=476, [2M+Na]=973

Step D: Synthesis of dibutyl 1-(N,N-diethylhexylcarbamoyl)nonylphosphonate

To a three-necked flask under agitation and under nitrogen are added 1.99 g (1 eq.) of dibutyl 1-(N,N-diethylhexylcarbamoyl)methylphosphonate, 50 mL of tetrahydrofuran and a few crystals of 2,2'-bipyridine, that are cooled to −50° C. using a dry ice/acetone bath. 3.92 mL (1.5 eq.) of a 1.6 mol/L solution of n-butyllithium in hexane are added dropwise. A clear red reaction mixture is obtained which is left 20 minutes at this temperature. The addition is then made of 0.92 mL (1.25 eq.) of bromooctane. The dry ice/acetone bath is removed and the reaction gradually rises to ambient temperature. The reaction medium is heated overnight at 60° C. The reaction medium is then poured onto 100 mL of distilled water and acidified through the addition of 1 N HCl in a sufficient amount to obtain an acid pH. The aqueous phase is extracted with twice 50 mL of ethyl ether. The ether phases are washed with twice 50 mL of distilled water and 50 mL of NaCl-saturated water, dried over magnesium sulphate, filtered and evaporated to dryness in a rotary evaporator. The 3.45 g of yellow oil thus obtained are subjected to a silica column chromatography (125 g-63-200 μm particle size) using a mixture of cyclohexane/ethyl acetate 9:1 v/v as eluent.

This yields 1.1 g of dibutyl 1-(N,N-diethylhexylcarbamoyl)nonyl-phosphonate in the form of a colourless oil (Yield: 44%), for which the $^1$H, $^{13}$C and $^{31}$P NMR characterisations have already been given under item I.1.11 above.

Step E: Synthesis of butyl 1-(N,N-diethylhexylcarbamoyl)nonylphosphonate

In a CEM Discover™ microwave reactor 0.4 g (1 eq.) of 1-(N,N-diethylhexylcarbamoyl)dibutyl nonylphosphonate, 5 mL of distilled water, 5 mL of dimethylformamide and 0.23 g (6 eq.) of potash are added and heated to 150° C. for 15 hours. After this time the reaction medium is poured onto 100 mL of distilled water and acidified with the addition of 1 N HCl in a sufficient amount to obtain an acid pH. The aqueous phase is extracted with twice 50 mL of ethyl ether. The ether phases are washed with twice 50 mL of distilled water, dried over magnesium sulphate, filtered and evaporated to dryness in a rotary evaporator. The 0.34 g of oil obtained are subjected to silica column chromatography (17 g-63-200 μm particle size) using a dichloromethane/methanol 97:3 mixture v/v for elution.

In this manner 0.14 g of the title compound are obtained in the form of a colourless oil (Yield: 39%) for which the $^1$H, $^{13}$C and $^{31}$P NMR characterisations have already been given above under item I.1.11.

I.2.2—Other Compounds

The following compounds:
Ethyl 1-(N,N-diethylhexylcarbamoyl)benzylphosphonate, denoted DEHCBPE, which meets above particular formula (I-a) wherein m=0, $R^1=R^2$=2-ethylhexyl, $R^3$=phenyl, $R^4$=ethyl and $R^5$=H;

Ethyl 1-(N,N-diethylhexylcarbamoyl)ethylphosphonate denoted DEHCEPE, which meets above particular formula (I-a) wherein m=0, $R^1=R^2$=2-ethylhexyl, $R^3$=methyl, $R^4$=ethyl and $R^5$=H;

Ethyl 1-(N,N-diethylhexylcarbamoyl)nonylphosphonate, denoted DEHCNPE, which meets above particular formula (I-a) wherein m=0, $R^1=R^2$=2-ethylhexyl, $R^3$=n-octyl, $R^4$=ethyl and $R^5$=H; and Butyl 1-(N,N-dioctylcarbamoyl)nonylphosphonate, denoted DOCNPB, which meets above particular formula (I-a) wherein m=0, $R^1=R^2=R^3$=n-octyl, $R^4$=n-butyl and $R^5$=H;

are synthesised by performing steps A, B, D and E shown in FIG. 2, and by using for each of these steps an operating protocol similar to the protocol described under item I.2.1 above.

The synthesis is also performed of:
Ethyl 1-(N,N-diethylhexylcarbamoyl)methylphosphonate, denoted DEHCMPE, which meets above particular formula (I-a) wherein m=0, $R^1=R^2$=2-ethylhexyl, $R^3=R^5$=H and $R^4$=ethyl; and Butyl 1-(N,N-diethylhexylcarbamoyl)methylphosphonate, denoted DEHCMPB, which meets above particular formula (I-a) wherein m=0, $R^1=R^2$=2-ethylhexyl, $R^3=R^5$=H and $R^4$=n-butyl;

by performing steps A, B and C shown in FIG. 2, and by using for steps A and B an operating protocol similar to the protocol described under item I.2.1 above, and for step C an operating protocol similar to the one described under item I.2.1 above for step E.

I.3—Synthesis of the Compounds of Particular Formula (I-b)

Figure 3:
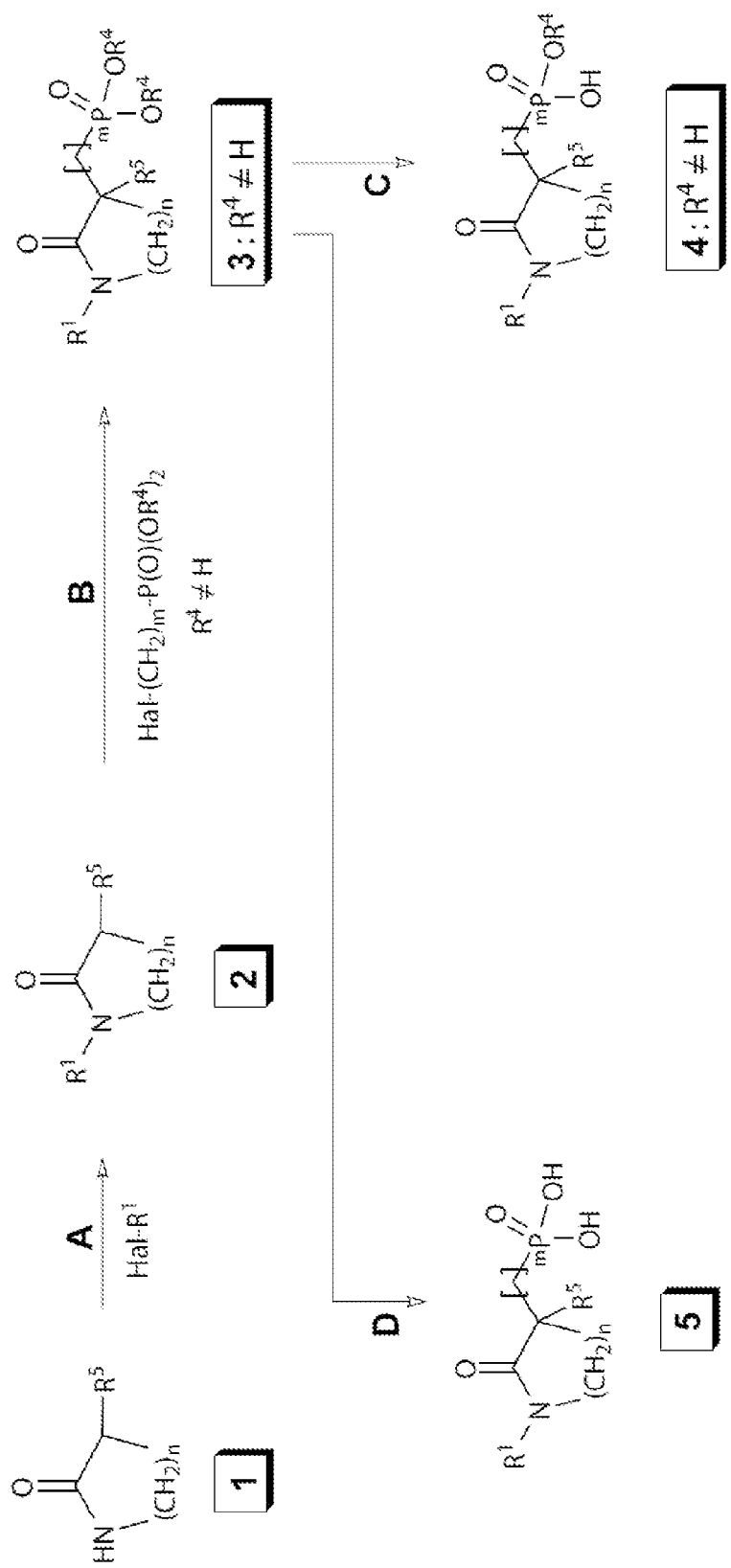
FIG. 3 illustrates the steps of methods for synthesising compounds of the invention which meet particular formula (I-b).

The compounds meeting above particular formula (I-b) wherein m, $R^1$, $R^4$ and $R^5$ have the same meaning as previously can be synthesised by following the reaction scheme illustrated in FIG. 3.

As can be seen in this Figure, for this synthesis at a first step denoted A, a lactame denoted 1 is caused to react with a halide (e.g. a bromide) Hal-$R^1$ to obtain compound 2.

At a second step denoted B in FIG. 3, compound 2 is caused to react with a compound Hal-$(CH_2)_m$—$P(O)(OR^4)_2$ (i.e. a halogenoalkylphosphonate if m differs from 0, and a halogenophosphonate if m=0) wherein $R^4$ differs from a hydrogen atom to obtain compound 3 wherein $R^4$ differs from a hydrogen atom.

Compound 3 obtained is then subjected:
either to a monosaponification step, denoted C in FIG. 3, which is performed in the same manner as step C in FIG. 2 described above, to obtain compound 4 wherein $R^4$ differs from a hydrogen atom;

or to a hydrolysis step, denoted D in FIG. 3, which is performed in the same manner as step E in FIG. 2 described above, to obtain compound 5 wherein $R^4$ is a hydrogen atom.

The synthesis of ethyl (N-dodecylpyrrolidone)-1-phosphonate, denoted DPPE, which meets particular formula (I-b) wherein m=0, $R^1$=n-dodecyl, $R^2$ and $R^3$ together form a —$CH_2$—$CH_2$— group, $R^4$=ethyl, $R^5$=H, can therefore be obtained by performing steps A, B and C of the reaction scheme shown in FIG. 3.

Step A is conducted by adding tetrabutylammonium bromide (950 mg-3 mmol-0.05 eq.) and powder potash (23.1 g-411 mmol-7 eq.) under agitation to a solution of 2-pyrrolidinone (5.00 g-58.8 mmol) and bromododecane (18.5 mL, 76.4 mmol, 1.3 eq.) in toluene (60 mL). The mixture is heated to 50° C. overnight. After disappearance of the 2-pyrrolidinone (verified by TLC using a 4:1 v/v mixture of ethyl acetate and cyclohexane, and phosphomolybdic acid for detection) and cooling, 60 mL of water is added and the mixture left under agitation for a further 15 minutes. The aqueous and organic phases are separated and the aqueous phase is extracted once with diethylether (60 mL). The organic phases are combined, dried over $Na_2SO_4$, filtered and concentrated. After vacuum distillation (146° C.-0.5 mbars), N-dodecylpyrrolidin-2-one is obtained (Yield: 80%) for which the $^1H$ and $^{13}C$ NMR characterisations are as follows:

$^1H$ NMR (400 MHz, $CDCl_3$) δ (ppm): 0.88 (t, 3H, J=7.0 Hz, $CH_3$); 1.25-1.31 (m, 18H, $CH_2$); 1.47-1.54 (m, 2H, Alk-$CH_2$—$CH_2$—N); 1.97-2.05 (m, 2H, CO—$CH_2$—$CH_2$—$CH_2$—N); 2.38 (t, 2H, J=8.0 Hz, CO—$CH_2$—$CH_2$—$CH_2$—N); 3.26 (t, 2H, J=7.5 Hz, Alk-$CH_2$—$CH_2$—N); 3.37 (t, 2H, J=7.0 Hz, CO—$CH_2$—$CH_2$—$CH_2$—N).

$^{13}C$ NMR (100 MHz, $CDCl_3$) δ (ppm): 14.3 ($CH_3$); 18.1 (CO—$CH_2$—$CH_2$—$CH_2$—N); 22.9; 27.0 ($CH_{2alk}$); 27.5 (Alk-$CH_2$—$CH_2$—N); 29.5; 29.7; 29.8; 29.9 ($CH_{2alk}$); 31.3 (CO—$CH_2$—$CH_2$—$CH_2$—N); 32.1 ($CH_{2alk}$); 42.7 (Alk-$CH_2$—$CH_2$—N); 47.2 (CO—$CH_2$—$CH_2$—$CH_2$—N); 174.9 (CO).

Step B is conducted by adding dropwise and under agitation a solution of N-dodecylpyrrolidinone (1.91 g-7.5 mmol) in anhydrous THF (7.5 mL) to a solution of lithium diisopropylamide (7.5 mL-2M in THF) at −80° C. under argon. The mixture is left to return to ambient temperature and it is held under agitation for 1 hour. It is then cooled to −80° C. and diethyl chlorophosphate is added (1.25 mL-8.6 mmol). After 15 minutes, the mixture is left to return to ambient temperature and it is held under agitation overnight. The mixture is then acidified to pH 1 using a 1 mol/L HCl solution and extracted with dichloromethane (2×10 mL). The aqueous and organic phases are separated and the organic phase is dried over $Na_2SO_4$, filtered and concentrated. After purification by flash chromatography (ethyl acetate/acetone: from 100:0 to 20:80, v/v), diethyl (N-dodecyl-pyrrolidinone)-1-phosphonate is obtained (Yield: 37%) for which the $^1H$, $^{13}C$ and $^{31}P$ NMR characterisations are the following:

$^1H$ NMR (400 MHz, $CDCl_3$) δ (ppm): 0.89 (t, 3H, J=7.0 Hz, $CH_3$); 1.26-1.38 (m, 24H, $CH_2$, O—$CH_2$—$CH_3$); 1.49-1.56 (m, 2H, Alk-$CH_2$—$CH_2$—N); 2.25-2.47 (m, 2H, COCH(P)—$CH_2$—$CH_2$—N); 2.95 (ddd, 1H, J=22.0 Hz, 10.0 Hz, 5.5 Hz, COCH(P)—$(CH_2)_2$); 3.21-3.37 (m, 3H, COCH(P)—$CH_2$—$CH_2$—N, Alk-$CH_2$—N); 3.50-3.56 (qd, 1H, J=8.0 Hz, J=1.0 Hz, COCH(P)—$CH_2$—$CH_2$—N); 4.13-4.31 (m, 4H, 0-$CH_2$—$CH_3$).

$^{13}C$ NMR (100 MHz, $CDCl_3$) δ (ppm): 14.1 ($CH_3$); 16.4 ($CH_3$—$CH_2$—O); 20.5 (d, J=Hz, COCH(P)—$CH_2$—$CH_2$—N), 22.7; 26.8 ($CH_2$); 27.2 (Alk-$CH_2$—$CH_2$—N); 29.3; 29.4; 29.5; 31.9 ($CH_2$); 40.5; 41.9 (d, J=142 Hz, COCH(P)—$(CH_2)_2$N); 43.1 (Alk-$CH_2$—N); 43.8 (d, J=4.0 Hz, COCH(P)—$CH_2$—$CH_2$—N), 62.2 (d, J=6.5 Hz, O—$CH_2$—$CH_3$); 63.0 (d, J=6.5 Hz, O—$CH_2$—$CH_3$); 169.0 (d, J=4.0 Hz, C=O).

$^{31}P$ NMR (160 MHz, $CDCl_3$) δ (ppm): 24.7.

Step C is conducted using potash (4 eq. per 1 eq. of diethyl (N-dodecylpyrrolidinone)-1-phosphonate—reflux for 2.5 hours) and leads to ethyl (N-dodecylpyrrolidone)-1-phosphonate (Yield: 99%) for which the $^1H$, $^{13}C$ and $^{31}P$ NMR characterisations are the following:

¹H NMR (400 MHz, CDCl₃) δ (ppm): 0.89 (t, 3H, J=6.5 Hz, CH₃); 1.26-1.32 (m, 21H, CH₂, O—CH₂—CH₃); 1.44-1.51 (m, 2H, Alk-CH₂—CH₂—N); 2.21-2.44 (m, 2H, COCH(P)—CH₂—CH₂—N); 2.96 (ddd, 1H, J=22.0 Hz, 10.0 Hz, 5.5 Hz, COCH(P)—(CH₂)₂); 3.19-3.34 (m, 3H, COCH(P)—CH₂—CH₂—N, Alk-CH₂—N); 3.45-3.51 (q, 1H, J=8.0 Hz, COCH(P)—CH₂—CH₂—N); 4.11-4.19 (m, 2H, O—CH₂—CH₃).

¹³C NMR (100 MHz, CDCl₃) δ (ppm): 14.1 (CH₃; 16.4 (d, J=6.0 Hz, CH₃—CH₂—O); 20.5 (d, J=3.0 Hz, COCH(P)—CH₂—CH₂—N), 22.7; 26.8 (CH₂); 27.2 (Alk-CH₂—CH₂—N); 29.3; 29.4; 29.5; 29.6; 31.9 (CH₂); 40.5; 41.9 (d, J=142 Hz, COCH(P)—(CH₂)₂N); 43.2 (Alk-CH₂—N); 46.0 (d, J=4.5 Hz, COCH(P)—CH₂—CH₂—N), 62.3 (d, J=6.5 Hz, O—CH₂—CH₃); 170.0 (d, J=4.0 Hz, C=O).

³¹P NMR (160 MHz, CDCl₃) δ (ppm): 24.9.

EXAMPLE II

Properties of the Compounds of the Invention

II.1—Capacity of the Compounds of the Invention to Extract Uranium from a Synthetic Solution of U—Fe in 5 M H₃PO₄

The capacity of the compounds of the invention to extract uranium from an aqueous solution of phosphoric acid is assessed by extraction tests performed in the following manner.

Each tested compound is first solubilised in n-dodecane (without using a phase modifying agent or heating) in a concentration of 0.25 mol/L.

6 mL of each of the organic phases obtained are contacted and held under agitation for 1 hour at ambient temperature (23-24° C.), with 6 mL of a synthetic aqueous phase comprising 5 mol/L phosphoric acid, 0.25 g/L of uranium (VI) and 2.5 g/L of iron(III).

These phases are then separated by gravity settling in less than 3 minutes.

The concentrations of uranium(VI) and iron(III) are measured:
- in the initial aqueous phase before it is contacted with the organic phases, via X fluorescence and Inductively Coupled Plasma Atomic Emission Spectrometry (ICP-AES),
- in the aqueous phases obtained after their separation from the organic phases, also by X fluorescence and ICP-AES; and
- in the organic phases obtained after their separation from the aqueous phases by X fluorescence.

Table I below, for each tested compound, gives the distribution coefficient of uranium(VI), denoted $D_U$, and the separation factor between uranium(VI) and iron(III), denoted $FS_{U/Fe}$, which are obtained from the uranium and iron contents thus measured.

This Table also specifies the distribution coefficient $D_U$ and $FS_{U/Fe}$ separation factor which are obtained under the same conditions with the synergic HDEHP/TOPO mixture.

It is recalled that in the field of liquid-liquid extractions, the distribution coefficient $D_M$ of an element M corresponds to the ratio of concentrations of this element in the organic and aqueous phases placed in contact with each other, and that the separation factor $FS_{M1/M2}$ between two metal elements M1 and M2 corresponds to $D_{M1}/D_{M2}$, i.e. to the ratio of the distribution coefficients of the metal elements M1 and M2 obtained during one same extraction.

TABLE I

| Compounds | $D_U$ | $FS_{U/Fe}$ |
|---|---|---|
| HDEHP/TOPO | 3.8 | 200 |
| DEHCMPE | 12.2 | 10 |
| DEHCMPB | 24 | 10 |
| DEHCBPE | 65 | 1 800 |
| DEHCEPE | 120 | 800 |
| DEHCNPE | 120 | 1 900 |
| DEHCNPB | 117 | 2 800 |
| DOCNPB | 116 | 400 |

This Table shows that the compounds of the invention have a capacity to extract uranium(VI) from an aqueous solution of phosphoric acid that is much higher than that of the synergic HDEHP/TOPO mixture, and that the majority of these compounds have U/Fe selectivity which is also much higher than that of the synergic HDEHP/TOPO mixture.

II.2—Influence of the Concentration at which the Compounds of the Invention are Used on their Extracting Properties The influence of the concentration at which the compounds of the invention are used on their extracting properties is assessed by extraction tests performed in the same manner as under item II.1 above, but using these compounds at different concentrations in the organic phases.

These tests were conducted with the 5 compounds of the invention which exhibited the best performance in the preceding tests.

Table II below gives the distribution coefficients $D_U$ and the $FS_{U/Fe}$ separation factors obtained for each of the tested compounds, and for one same compound, with each of the concentrations at which it was used.

This Table also specifies the distribution coefficients $D_U$ and the $FS_{U/Fe}$ separation factors obtained under the same conditions and at the same concentrations with the synergic HDEHP/TOPO mixture, and the ratios between the $D_U$ and $FS_{U/Fe}$ values obtained with the compounds of the invention and with this mixture.

TABLE II

| Compounds | [C] (mol/L) | $D_U$ | $FS_{U/Fe}$ | $D_U$ Ratio | $FS_{U/Fe}$ Ratio |
|---|---|---|---|---|---|
| TOPO/HDEHP | 0.25 | 3.8 | 150 | / | / |
|  | 0.1 | 0.8 | 230 |  |  |
| DEHCBPE | 0.25 | 67 | 1 450 | 18 | 9.7 |
|  | 0.1 | 16 | 1 740 | 20 | 7.6 |
| DEHCEPE | 0.25 | 120 | 800 | 32 | 4 |
|  | 0.1 | 71 | 2 800 | 89 | 14 |
| DEHCNPE | 0.25 | 120 | 1 900 | 32 | 9.5 |
|  | 0.1 | 75 | 9 400 | 90 | 47 |
|  | 0.05 | 23 | 26 000 | / | / |
| DEHCNPB | 0.25 | 117 | 2 800 | 31 | 14 |
|  | 0.1 | 70 | 8 700 | 88 | 43.5 |
|  | 0.05 | 20 | 30 000 | / | / |
| DOCNPB | 0.25 | 116 | 400 | 30 | 2 |
|  | 0.1 | 62 | 1 000 | 77 | 5 |
|  | 0.05 | 20 | 1 300 | / | / |

This Table shows that the ratios between the distribution coefficients $D_U$ obtained with the compounds of the invention and those obtained with the reference HDEHP/TOPO mixture are higher the lower the concentration at which these compounds and this mixture are used.

At a concentration of 0.1 mol/L, the DEHCNPE compound is 90 times more efficient and 47 times more selective than the TOPO/HDEHP mixture.

Figure 4:
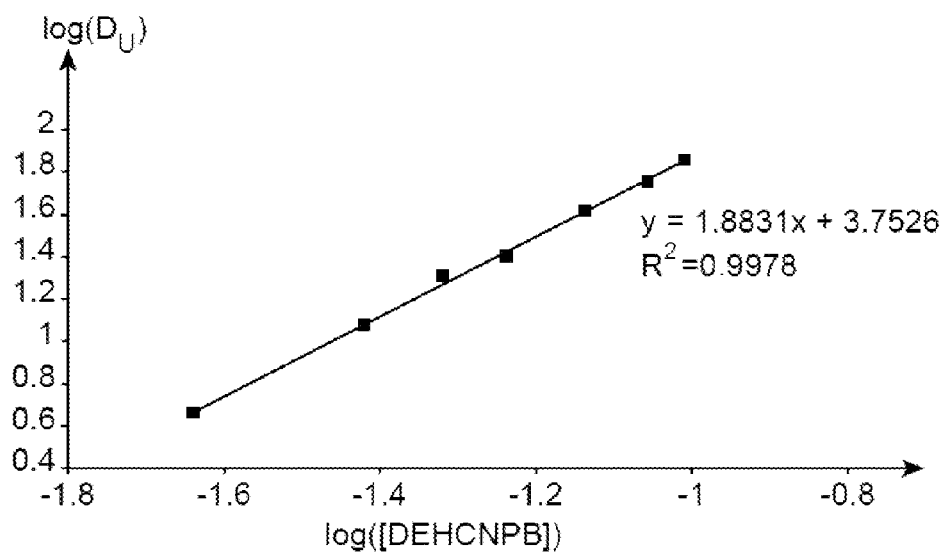
FIG. 4 illustrates the variation in the logarithm of the distribution coefficient of uranium(VI), denoted $\log(D_U)$, such as obtained during extractions performed with a compound of the invention, as a function of the logarithm of the molar concentration of this compound in the organic phase, denoted $\log([DEHCNPB])$.

The variation in the logarithm of the distribution coefficient of U(VI), denoted $\log(D_U)$, as a function of the logarithm of the molar concentration of compound DEHCNPB in the organic phase, denoted $\log([DEHCNPB])$, which is illustrated in FIG. 4, gives a slope of about 2, which shows that the $UO_2^{2+}$ ion would be extracted by the DEHCNPB compound in the form of a 1:2 complex.

Uranium/iron selectivity therefore reaches the value of 30 000 with the DEHCNPB compound when it is used at a concentration of 0.05 mol/L.

II.3—Influence of the Initial Concentration of Uranium(VI) in the Aqueous Solution of Phosphoric Acid on the Extrating Properties of the Compounds of the Invention The influence of the concentration of uranium(VI) in the initial aqueous solution of phosphoric acid on the extracting properties of compounds of the invention is assessed by extraction tests performed in the same manner as described under item II.1 above, but by varying the initial concentration of uranium(VI) in the aqueous phase.

These tests were performed with the DEHCPNB compound, at a concentration of 0.1 mol/L, having regard to its good performance.

With 0.1 mol/L of the DEHCPNB compound in n-dodecane, no third phase was observed, even at a uranium(VI) concentration of 5 g/L in the organic phase, which corresponds to 15 g/L of uranium(VI) in the initial aqueous phase.

Figure 5:
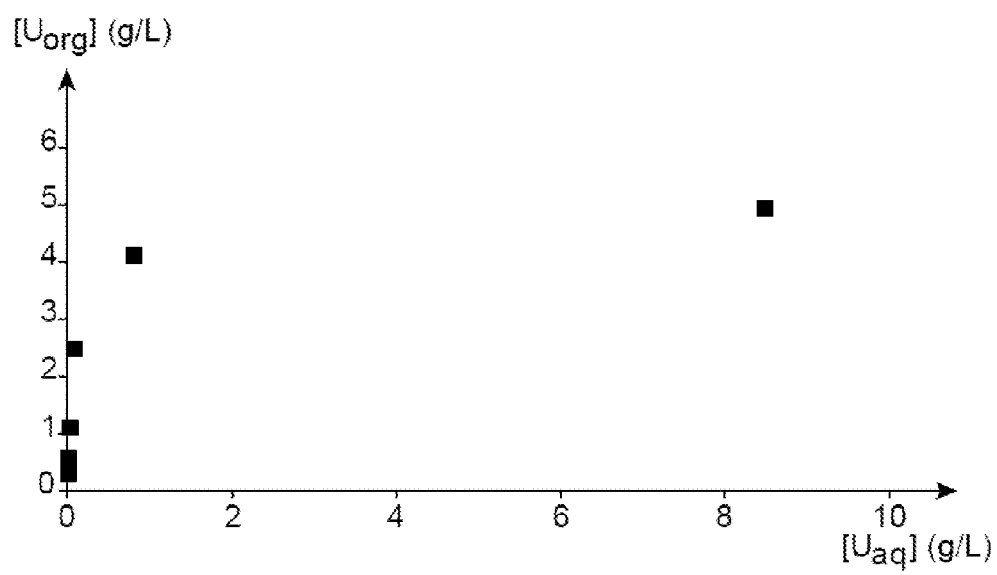
FIG. 5 illustrates the partition isotherm of uranium(VI), i.e. the trend in concentration of uranium in the organic phase, denoted $[U_{org}]$, as a function of the concentration of this element in aqueous phase, denoted $[U_{aq}]$), such as obtained during extractions conducted with a compound of the invention.

The results are given in FIG. 5 which shows that the concentration of uranium(VI) in aqueous phase($[U_{aq}]$) is lower than the concentration of uranium(VI) in organic phase ($[U_{org}]$) over a range of uranium(VI) concentration in an organic phase of less than 4.5 g/L of uranium(VI). Within this range the distribution coefficient $D_U$ observed is higher than 1.

This example illustrates the possibility of applying concentration schemes when extracting uranium contained in aqueous solutions of phosphoric acid derived from natural phosphates, using the DEHCPNB compound.

II.4—Influence of the Initial Concentration of Phosphoric Acid in the Aqueous Solution of Phosphoric Acid on the Extracting Properties of the Compounds of the Invention The influence of the concentration of phosphoric acid in the initial aqueous solution of phosphoric acid on the extracting properties of the compounds of the invention is assessed by extraction tests performed in the same manner as under item II.1 above, but using an aqueous phase containing 10 times more uranium than the phase used under item II.1 above, i.e. 2.5 g/L of uranium, by varying the initial concentration of phosphoric acid in the aqueous phase.

These tests were performed with the DEHCPNB compound at a concentration of 0.1 mol/L.

Figure 6:
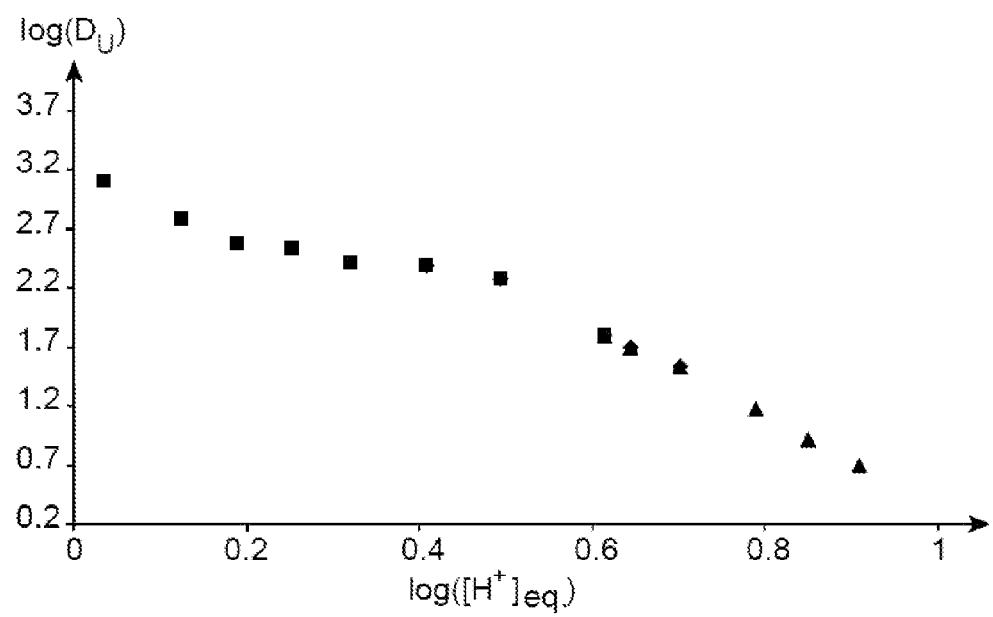
FIG. 6 illustrates the trend in the logarithm of the distribution coefficient of uranium(VI), denoted $\log(D_U)$, such as obtained during extractions performed with a compound of the invention, as a function of the logarithm of the molar concentration of acid in the aqueous phase in equilibrium after extraction, denoted $\log([H^+]_{eq.})$. The change in symbol in the Figure evidences the change of slope.

The variation in the logarithm of the distribution coefficient of uranium(VI) denoted $\log(D_U)$, as a function of the logarithm of the molar concentration of acid in equilibrium after extraction, denoted $\log([H^+]_{\acute{e}q.})$, which is illustrated in FIG. 6, shows that the extraction of uranium(VI) decreases when the concentration of phosphoric acid increases from 0.01 to 9 mol/L due to the competition between the $H^+$ and $UO_2^{2+}$ ions. Nevertheless, a distribution coefficient $D_U$ of 3.3 is obtained with a concentration of phosphoric acid of 9 mol/L, which should allow uranium(VI) to be extracted from aqueous solutions having high concentrations of phosphoric acid.

This example illustrates the possibility of operating over a wide range of acidities to extract uranium(VI) from an aqueous solution of phosphoric acid using the DEHCPNB compound.

II.5—Stripping of the Uranium(VI) Contained in an Organic Phase Comprising a Compound of the Invention Stripping tests were performed using:
a plurality of organic phases comprising 0.01 to 0.1 mol/L of DEHCNPB compound in n-dodecane which were previously loaded with uranium(VI) and iron by contact with a solution comprising 5 mol/L phosphoric acid, 0.25 g/L of uranium(VI) and 2.5 g/L or iron(III) in water; and
an aqueous phase comprising 0.5 mol/L of ammonium carbonate $(NH_4)_2CO_3$.

For this purpose, 6 mL of each of the organic phases (which contain most of the uranium(VI) initially contained in the solution from which it was extracted, and traces of iron) were placed in contact and held under agitation for 1 hour at ambient temperature (23-24° C.), with 6 mL of aqueous phase.

These phases were subsequently separated by gravity settling in less than 3 minutes.

As previously the concentrations of uranium(VI) and iron(III) were measured:
in the aqueous phase before it was contacted with the organic phases, by X fluorescence and ICP-AES;
in the aqueous phases obtained after separation from the organic phases, also by X fluorescence and ICP-AES; and
in the organic phases obtained after separation from the aqueous phases, by X fluorescence.

The results show that the distribution coefficients of uranium are lower than 0.1, which means that the entirety of the uranium contained in the organic phases is found in the aqueous phases after a single contact between aqueous phase and organic phase, and without the onset of a third phase or turbidity.

The DEHCNPB compound should therefore allow the overcoming of problems related to the presence of iron(III) in the aqueous solutions of phosphoric acid obtained from natural phosphates whilst improving the extraction of uranium(VI) from these solutions compared with extraction using the synergic HDEHP/TOPO mixture.

II.6—Extraction Kinetics

The extraction kinetics of uranium(VI) with the compounds of the invention were assessed by extraction tests performed in the same manner as under item II.1 above, but by controlling the continuous aqueous phase (CAP) and using an aqueous phase containing 10 times more uranium than the phase used under II.1 above. This aqueous phase therefore contains 5 mol/L phosphoric acid, 2.5 g/L uranium and 2.5 g/L iron.

The organic and aqueous phases were placed in contact in a 25 mL cell with double jacket, thermostat-controlled at 25° C., under agitation with an anti-vortex baffle plate (2000 rpm).

These tests were performed with the DEHCPNB compound, at a concentration of 0.1 mol/L.

Figure 7:
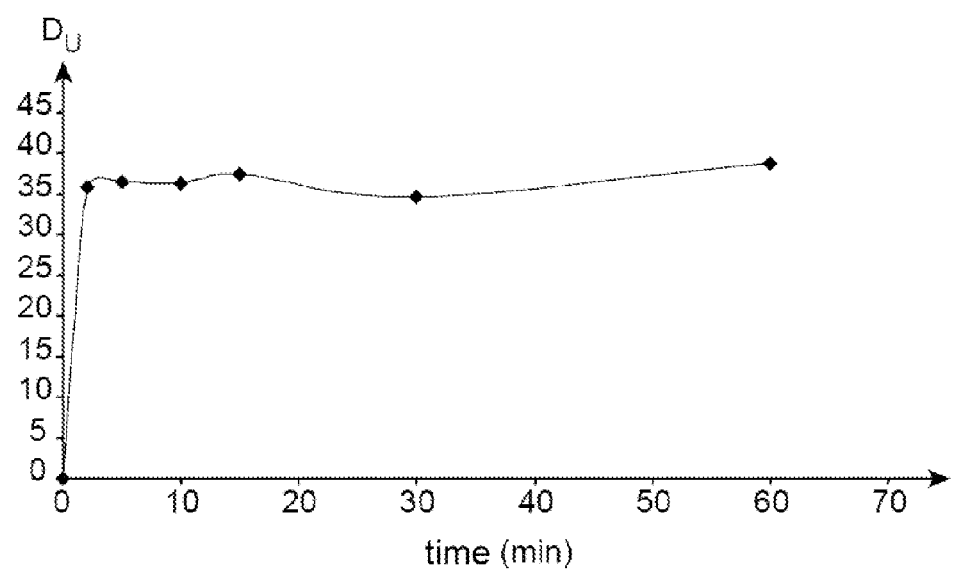
FIG. 7 illustrates the trend in the distribution coefficient of uranium (VI), denoted $D_U$, such as obtained during extractions performed with a compound of the invention, as a function of contact time, expressed in minutes, between the aqueous and organic phases.

The results are illustrated in FIG. 7 which shows that extraction equilibrium is rapidly reached in less than two minutes.

The extraction kinetics of uranium(VI) using the DEHC-NPB compound do not therefore amount to a limiting factor and allow envisaging of the use of this compound as extractant in industrial extractors with short residence time.

II.7—Selectivity of Uranium(VI) Extraction Versus Other Metal Cations

The selectivity of uranium(VI) extraction in relation not only to iron but also to other metal cations which may be contained in aqueous solutions of phosphoric acid obtained from natural phosphates, is assessed by performing an extraction test in the same manner as under item II.1 above, but by using as aqueous phase a solution derived from digestion of a natural phosphate with sulphuric acid.

This aqueous phase comprises 5 mol/L of phosphoric acid. Its metal cation composition is given in Table III below.

As organic phase, a phase is used containing the DEHCPNB compound, at a concentration of 0.1 mol/L, in n-dodecane.

In this test the cation content was measured by ICP-AES in the initial aqueous phase before it was contacted with the organic phase, and in the aqueous phase obtained after extraction, i.e. after its separation from the organic phase.

The distribution coefficients $D_M$ obtained for uranium(VI) and for each of the other metal cations are given in Table III below.

TABLE III

| | Initial aqueous phase | |
|---|---|---|
| Cations | [C] mg/L | $D_M$ after extraction |
| U | 155 | >150 |
| Fe | 2470 | 0.01 |
| As | 16 | <0.07 |
| Mo | 6 | 0.15 |
| Cr | 276 | <0.01 |
| Zn | 393 | <0.01 |
| Cd | 19 | <0.06 |
| W | 14 | <0.07 |
| Al | 1880 | <0.01 |
| V | 264 | <0.02 |
| Ti | 55 | <0.02 |
| Zr | 44 | <0.03 |

As shown in this Table, at a concentration of 0.1 mol/L, the DEHCNPB compound exhibits a capacity to extract uranium(VI) from an aqueous solution of phosphoric acid obtained from a natural phosphate, that is comparable with the capacity observed with a synthetic solution.

Amongst the major impurities, aluminum and iron, solely the latter was extracted in quantifiable manner although at low level.

Amongst the minor impurities, only molybdenum was extracted in measurable amounts, these also being low.

The DEHCNPB compound therefore displays excellent selectivity for uranium(VI) versus other metal cations which may be contained in an aqueous solution of phosphoric acid obtained from a natural phosphate.

II.8—Example of Embodiment of Continuous Operation of the Method of the Invention A test for continuous operation of the method of the invention was performed on pilot scale, using laboratory mixer-settler units.

The objective of this test was to verify the performance of uranium(VI) extraction and more particularly the selectivity of the solvent for iron, a majority element contained in ores. It was more particularly sought to obtain a concentrated solution of uranium(VI) from an aqueous solution of phosphoric acid, characterized in that the iron content is less than 0.15%.

Figure 8:
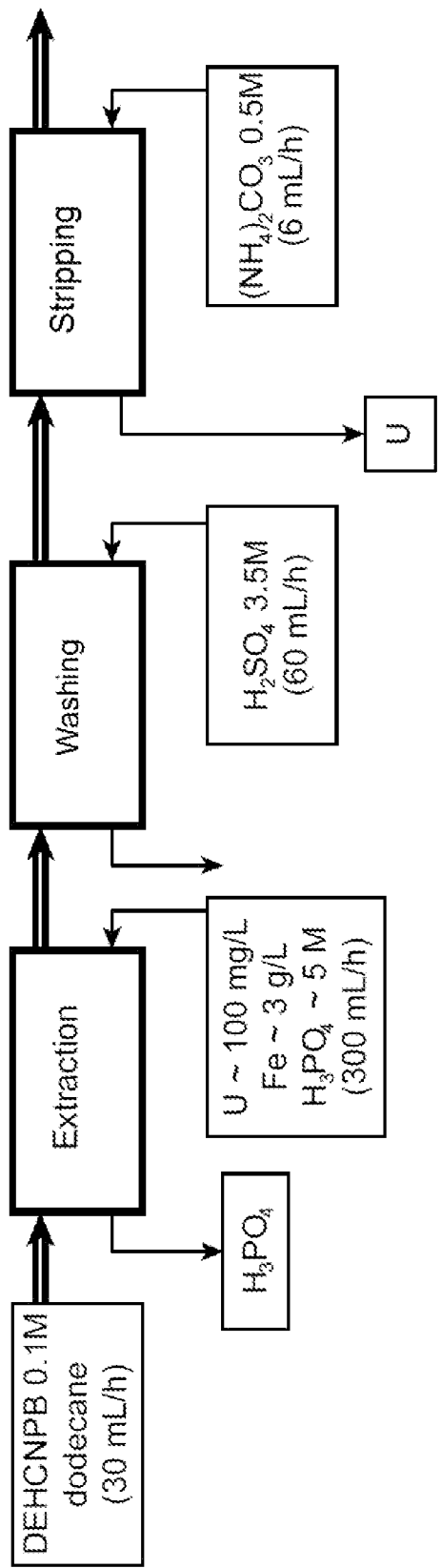
FIG. 8 gives a schematic followed to test continuous operation of the method of the invention on a pilot scale using laboratory mixer-settlers.

The operating scheme illustrated in FIG. 8 comprised 3 steps:

an extracting step of the uranium contained in the aqueous solution of phosphoric acid, this extraction being 5-stage extraction using the DEHCNPB compound at a concentration of 0.1 mol/L in n-dodecane;

a washing step of the organic phase obtained after this extraction, this washing being 3-stage washing performed using an aqueous solution of sulphuric acid; and a concentrating stripping step of the uranium(VI) contained in the organic phase obtained after this washing, this stripping being 3-stage stripping using an aqueous solution of ammonium carbonate.

The extraction and wash steps were conducted at 40° C. whilst the stripping step was conducted at 45° C.

The piloting of the method was ensured by monitoring the concentrations of uranium and iron in the aqueous solutions leaving the three mixer-settler units and from the organic phase derived from the mixer-settler dedicated to extraction.

The test was performed on an industrial solution of phosphoric acid having a uranium concentration of 119 mg/L, an iron concentration of 5.7 g/L and acidity of 5.2 mol/L.

The results of this test conform to the objectives that were set, namely a concentrated solution of uranium was obtained ([U]~5 g/L in the uranium production flow derived from the stripping step) with an iron content (~2.4 mg/L) much lower than the targeted 0.15 weight % compared with uranium (<0.05%).

CITED REFERENCES

[1] U.S. Pat. No. 3,711,591
[2] FR 2 396 803
[3] FR 2 596 383
[4] U.S. Pat. No. 4,316,877
[5] FR 2 460 958
[6] FR 2 460 960
[7] FR 2 604 919

The invention claimed is:

1. A compound of general formula (I) below:

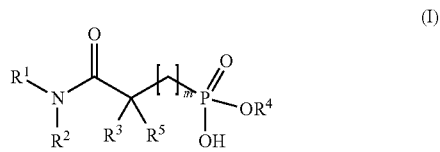

where:
m is an integer of 0, 1 or 2;
$R^1$ and $R^2$, the same or different, are a saturated or unsaturated, straight-chain or branched hydrocarbon group having 6 to 12 carbon atoms;
$R^3$ is:
a saturated or unsaturated, straight-chain or branched hydrocarbon group having 1 to 12 carbon atoms and optionally one or more heteroatoms;

a saturated or unsaturated, monocyclic hydrocarbon group having 3 to 8 carbon atoms and optionally one or more heteroatoms; or a monocyclic aryl or heteroaryl group;

or else $R^2$ and $R^3$ together form a —$(CH_2)_n$— group wherein n is an integer from 1 to 4;

$R^4$ is a saturated or unsaturated, straight-chain or branched hydrocarbon group having 2 to 8 carbon atoms, or a monocyclic aromatic group; and $R^5$ is a hydrogen atom or a saturated or unsaturated, straight-chain or branched hydrocarbon group having 1 to 12 carbon atoms.

2. The compound of claim 1 wherein the compound is of particular formula (I-a) below:

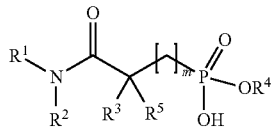

(I-a)

wherein:

m, $R^1$, $R^4$ and $R^5$ are such as previously defined;

$R^2$ is a saturated or unsaturated, straight-chain or branched hydrocarbon group having 6 to 12 carbon atoms; whilst $R^3$ is:

a saturated or unsaturated, straight-chain or branched hydrocarbon group having 1 to 12 carbon atoms and optionally one or more heteroatoms;

a saturated or unsaturated, monocyclic hydrocarbon group having 3 to 8 carbon atoms and optionally one or more heteroatoms; or a monocyclic aryl or heteroaryl group.

3. The compound of claim 2, wherein $R^1$ and $R^2$, the same or different, are a straight-chain or branched alkyl group having 6 to 12 carbon atoms.

4. The compound of claim 3, wherein $R^1$ and $R^2$ are the same and each are a branched alkyl group having 8 to 10 carbon atoms.

5. The compound of claim 4, wherein $R^1$ and $R^2$ are a 2-ethylhexyl group.

6. The compound of claim 2, wherein m equals 0.

7. The compound of claim 2, wherein $R^3$ is a straight-chain or branched alkyl group having 1 to 12 carbon atoms, or a monocyclic aromatic group.

8. The compound of claim 2, wherein $R^5$ is a hydrogen atom.

9. The compound of claim 7, wherein $R^3$ is a methyl group, an n-octyl group or a phenyl group.

10. The compound of claim 2, wherein $R^4$ is a straight-chain or branched alkyl group having 2 to 8 carbon atoms.

11. The compound of claim 10, wherein $R^4$ is a straight-chain or branched alkyl group having 2 to 4 carbon atoms.

12. The compound of claim 11, wherein $R^4$ is an ethyl group or an n-butyl group.

13. The compound of claim 2, wherein the compound is:

Ethyl 1-(N,N-diethylhexylcarbamoyl)benzylphosphonate, wherein m equals 0, $R^1$ and $R^2$ each are a 2 ethylhexyl group, $R^3$ is a phenyl group, $R^4$ is an ethyl group and $R^5$ is a hydrogen atom;

Ethyl 1-(N,N-diethylhexylcarbamoyl)ethylphosphonate, wherein m equals 0, $R^1$ and $R^2$ each are a 2-ethylhexyl group, $R^3$ is a methyl group, $R^4$ is an ethyl group and $R^5$ is a hydrogen atom;

Ethyl 1-(N,N-diethylhexylcarbamoyl)nonylphosphonate, wherein m equals 0, $R^1$ and $R^2$ each are a 2 ethylhexyl group, $R^3$ is an n-octyl group, $R^4$ is an ethyl group and $R^5$ is a hydrogen atom;

Butyl 1-(N,N-diethylhexylcarbamoyl)nonylphosphonate, wherein m equals 0, $R^1$ and $R^2$ each are a 2 ethylhexyl group, $R^3$ is an n-octyl group, $R^4$ is an n-butyl group and $R^5$ is a hydrogen atom; or Butyl 1-(N,N-dioctylcarbamoyl)nonylphosphonate, wherein m equals 0, $R^1$, $R^2$ and $R^3$ each are an n-octyl group, $R^4$ is an n-butyl group and $R^5$ is a hydrogen atom.

14. The compound of claim 13, which is ethyl 1-(N, N-diethylhexylcarbamoyl)nonylphosphonate or butyl 1-(N, N-diethylhexylcarbamoyl)nonyl-phosphonate.

15. The compound of claim 1, wherein the compound is of particular formula (I-b):

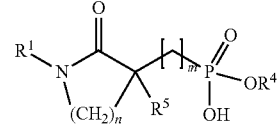

(I-b)

wherein m, n, $R^1$, $R^4$ and $R^5$ are such as previously defined.

16. The compound of claim 15, wherein $R^1$ is a straight-chain or branched alkyl group having 6 to 12 carbon atoms.

17. The compound of claim 15, wherein m equals 0, $R^4$ is a straight-chain or branched alkyl group having 2 to 8 carbon atoms and $R^5$ is a hydrogen atom.

18. The compound of claim 15, which is ethyl (N-dodecylpyrrolidone)-1-phosphonate wherein m=0, n=2, $R^1$ is an n-dodecyl group, $R^4$ is an ethyl group and $R^5$ is a hydrogen atom.

19. A method for extracting uranium(VI) from an aqueous solution of phosphoric acid, comprising contacting the aqueous solution with an organic phase comprising a compound of general formula (I) below:

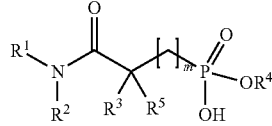

(I)

where:

m is an integer of 0, 1 or 2;

$R^1$ and $R^2$, the same or different, are a saturated or unsaturated, straight-chain or branched hydrocarbon group having 6 to 12 carbon atoms;

$R^3$ is:

a saturated or unsaturated, straight-chain or branched hydrocarbon group having 1 to 12 carbon atoms and optionally one or more heteroatoms;

a saturated or unsaturated, monocyclic hydrocarbon group having 3 to 8 carbon atoms and optionally one or more heteroatoms; or a monocyclic aryl or heteroaryl group;

or else $R^2$ and $R^3$ together form a —$(CH_2)_n$— group wherein n is an integer from 1 to 4;

$R^4$ is, a saturated or unsaturated, straight-chain or branched hydrocarbon group having 2 to 8 carbon atoms, or a monocyclic aromatic group; and R⁵ is a hydrogen atom or a saturated or unsaturated, straight-chain or branched hydrocarbon group having 1 to 12 carbon atoms, and then separating the aqueous solution from the organic phase.

20. The method of claim 19, wherein the aqueous solution contains 0.01 to 9 mol/L of phosphoric acid.

21. The method of claim 20, wherein the aqueous solution is derived from the digestion of a natural phosphate with sulphuric acid.

22. A method for recovering uranium contained in an aqueous solution of phosphoric acid derived from the digestion of a natural phosphate with sulphuric acid, comprising:
   a) extracting the uranium, in oxidation state VI, from the aqueous solution of phosphoric acid by contacting the aqueous solution with an organic phase comprising a compound of general formula (I) below:

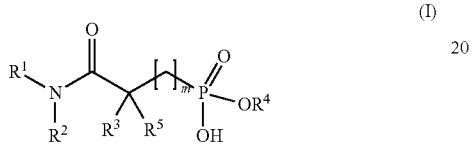

(I)

where:
   m is an integer of 0, 1 or 2;
   $R^1$ and $R^2$, the same or different, are a saturated or unsaturated, straight-chain or branched hydrocarbon group having 6 to 12 carbon atoms;
   $R^3$ is:
   a saturated or unsaturated, straight-chain or branched hydrocarbon group having 1 to 12 carbon atoms and optionally one or more heteroatoms;
   a saturated or unsaturated, monocyclic hydrocarbon group having 3 to 8 carbon atoms and optionally one or more heteroatoms; or
   a monocyclic aryl or heteroaryl group;
   or else $R^2$ and $R^3$ together form a —$(CH)_n$— group wherein n is an integer from 1 to 4;
   $R^4$ is, a saturated or unsaturated, straight-chain or branched hydrocarbon group having 2 to 8 carbon atoms, or a monocyclic aromatic group; and
   $R^5$ is a hydrogen atom or a saturated or unsaturated, straight-chain or branched hydrocarbon group having 1 to 12 carbon atoms such as defined in claim 1, then by separating the aqueous solution from the organic phase;
   b) washing the organic phase obtained at the end of step a);
   c) stripping the uranium(VI) contained in the organic phase obtained at the end of step b) by contacting the organic phase with an aqueous solution comprising a carbonate, then separating the organic phase and the aqueous solution; and optionally:
   d) acidifying the organic phase obtained at the end of step c) by contacting the organic phase with an acid aqueous solution.

23. The method of claim 22, wherein the compound is used in solution, at a concentration of 0.01 to 1 mol/L, in an organic diluent.

24. The method of claim 22, or claim 21, wherein the aqueous solution of phosphoric acid comprises 0.01 to 9 mol/L of phosphoric acid.

25. The method of claim 22, wherein the aqueous solution comprising the carbonate comprises 0.1 to 1.5 mol/L of carbonate.

* * * * *